US012700504B2

(12) United States Patent
Huang et al.

(10) Patent No.: US 12,700,504 B2
(45) Date of Patent: Aug. 4, 2026

(54) ESTIMATION DEVICE, ESTIMATION SYSTEM, ESTIMATION METHOD, AND RECORDING MEDIUM

(71) Applicant: NEC Corporation, Tokyo (JP)

(72) Inventors: Chenhui Huang, Tokyo (JP); Zhenwei Wang, Tokyo (JP); Kenichiro Fukushi, Tokyo (JP); Fumiyuki Nihey, Tokyo (JP); Hiroshi Kajitani, Tokyo (JP); Kentaro Nakahara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 58 days.

(21) Appl. No.: 18/560,462

(22) PCT Filed: May 21, 2021

(86) PCT No.: PCT/JP2021/019305
§ 371 (c)(1),
(2) Date: Nov. 13, 2023

(87) PCT Pub. No.: WO2022/244222
PCT Pub. Date: Nov. 24, 2022

(65) Prior Publication Data
US 2024/0257975 A1     Aug. 1, 2024

(51) Int. Cl.
*G16H 50/20*     (2018.01)
*A61B 5/00*      (2006.01)
(Continued)

(52) U.S. Cl.
CPC ........... *G16H 50/20* (2018.01); *A61B 5/1036* (2013.01); *A61B 5/1121* (2013.01); (Continued)

(58) Field of Classification Search
CPC ........ G16H 50/20; G16H 50/30; G16H 50/70; A61B 5/1036; A61B 5/1121; A61B 5/6807; A61B 5/743
See application file for complete search history.

(56) References Cited

U.S. PATENT DOCUMENTS

2002/0040601 A1*   4/2002   Fyfe .................. A63B 69/0028
                                                    73/488
2008/0133171 A1*   6/2008   Feichtinger .......... G01C 22/006
                                                    702/141
(Continued)

FOREIGN PATENT DOCUMENTS

JP      2008-161228  A      7/2008
JP      2010-017447  A      1/2010
(Continued)

OTHER PUBLICATIONS

Mitschke et al., "A Single Gyroscope Can Be Used to Accurately Determine Peak Eversion Velocity during Locomotion at Different Speeds and in Various Shoes," Appl. Sci. 2017, 7, 659; doi: 10.3390/app7070659. (Year: 2017).*
(Continued)

*Primary Examiner* — Jonathon A. Szumny
(74) *Attorney, Agent, or Firm* — Sughrue Mion, PLLC

(57)     ABSTRACT

An estimation device including a feature amount extraction unit that extracts, from a gait waveform extracted from time series data of sensor data based on a motion of a foot of a user, a feature amount according to an attribute of the user in a section in which a feature of a physical condition according to the attribute of the user appears; and estimates the physical condition of the user using the feature amount extracted according to the attribute of the user.

12 Claims, 25 Drawing Sheets

(51) Int. Cl.

| | |
|---|---|
| *A61B 5/103* | (2006.01) |
| *A61B 5/11* | (2006.01) |
| *G16H 50/30* | (2018.01) |
| *G16H 50/70* | (2018.01) |

(52) U.S. Cl.

CPC ............ *A61B 5/6807* (2013.01); *A61B 5/743* (2013.01); *G16H 50/30* (2018.01); *G16H 50/70* (2018.01); *A61B 2503/08* (2013.01); *A61B 2560/045* (2013.01); *A61B 2560/0462* (2013.01); *A61B 2562/0219* (2013.01); *A61B 2562/0247* (2013.01)

(56) References Cited

U.S. PATENT DOCUMENTS

| | | | | |
|---|---|---|---|---|
| 2008/0190202 | A1 * | 8/2008 | Kulach | A63B 24/0062 |
| | | | | 73/514.01 |
| 2016/0100801 | A1 | 4/2016 | Clark et al. | |
| 2016/0249833 | A1 * | 9/2016 | Ronchi | G01C 22/006 |
| | | | | 702/141 |
| 2017/0354348 | A1 * | 12/2017 | Winter | A61B 5/6807 |
| 2018/0220935 | A1 * | 8/2018 | Tadano | A61B 5/11 |
| 2019/0082771 | A1 * | 3/2019 | Shin | G01L 5/0052 |
| 2020/0000373 | A1 * | 1/2020 | Agrawal | A61B 5/7405 |
| 2020/0357508 | A1 * | 11/2020 | Deleu | G16H 50/50 |
| 2021/0145318 | A1 * | 5/2021 | Oumnia | A61B 5/1038 |
| 2022/0409125 | A1 * | 12/2022 | Saxena | A61B 5/6828 |
| 2024/0090620 | A1 * | 3/2024 | Khan | A43B 3/48 |
| 2024/0115159 | A1 * | 4/2024 | Segal | A61B 5/4848 |

FOREIGN PATENT DOCUMENTS

| | | | | | |
|---|---|---|---|---|---|
| JP | 2019-005340 | A | 1/2019 | | |
| WO | 2015/190042 | A1 | 12/2015 | | |
| WO | 2017/065241 | A1 | 4/2017 | | |
| WO | 2018/164157 | A1 | 9/2018 | | |
| WO | 2019/181483 | A1 | 9/2019 | | |
| WO | WO-2019175899 | A1 * | 9/2019 | .......... | A61B 5/6831 |
| WO | WO-2019193301 | A1 * | 10/2019 | .......... | A61B 5/6807 |
| WO | 2020/202543 | A1 | 10/2020 | | |
| WO | 2020/230282 | A1 | 11/2020 | | |

OTHER PUBLICATIONS

Wu et al., "An Intelligent In-Shoe System for Gait Monitoring and Analysis with Optimized Sampling and Real-Time Visualization Capabilities," Sensors 2021, 21, 2869. https://doi.org/10.3390/s21082869. (Year: 2021).*

Hagedorn et al., "Factors affecting center of pressure in older adults: the Framingham Foot Study," Journal of Foot and Ankle Research 2013, 6:18; http://www.jfootankleres.com/content/6/1/18. (Year: 2013).*

Song et al., "Human Body Mixed Motion Pattern Recognition Method Based on Multi-Source Feature Parameter Fusion," Sensors 2020, 20, 537; doi: 10.3390/s20020537. (Year: 2020).*

International Search Report for PCT Application No. PCT/JP2021/019305, mailed on Jul. 27, 2021.

English translation of Written opinion for PCT Application No. PCT/JP2021/019305, mailed on Jul. 27, 2021.

* cited by examiner

Fig.24

ESTIMATION DEVICE 22

FEATURE AMOUNT EXTRACTION UNIT 225

INFERENCE UNIT 227

Fig.25

ESTIMATION DEVICE, ESTIMATION SYSTEM, ESTIMATION METHOD, AND RECORDING MEDIUM

This application is a National Stage Entry of PCT/JP2021/019305 filed on May 21, 2021, the contents of all of which are incorporated herein by reference, in their entirety.

TECHNICAL FIELD

The present disclosure relates to an estimation device or the like that estimates a physical condition based on sensor data measured with gait.

BACKGROUND ART

With increasing interest in healthcare that performs physical condition management, a service that measures features (also referred to as gait) included in a gait pattern and provides information related to the gait to a user has attracted attention. For example, a device has been developed in which a load measurement device or an inertial measurement device is mounted on footwear such as shoes and the gait of a user is analyzed. When the physical condition can be estimated based on the information about the gait, an appropriate measure can be taken according to the sign appearing in gait. For example, when the physical condition can be estimated based on the information about the gait, a measure related to the estimated physical condition can be taken.

PTL 1 discloses a system that determines a motion characteristic of a user using a measurement value measured by a motion sensor attached to a back face of footwear. The system of PTL 1 calculates intensity metrics such as pronation degree and pronation excursion using acceleration in three axial directions, and angular velocities and angles around the three axes.

PTL 2 discloses a method of analyzing data of plantar pressure to evaluate the presence or absence of an abnormality regarding the foot. In the method of PTL 2, data of plantar pressure for a predetermined time is acquired by a pressure sensor provided in an insole of a shoe. In the method of PTL 2, pronation foot/supination foot is evaluated based on data after gait processing such as a plantar pressure parameter, a foot pressure center parameter, and a time parameter obtained by analyzing data of plantar pressure for a predetermined time.

PTL 3 discloses a gait motion analysis device that analyzes a gait motion using an image of a pedestrian imaged from multiple directions. The device of PTL 3 generates a silhouette image from a difference in value between a pixel at a position of a pedestrian appearing in an image and a pixel at a position related to the pedestrian in a background image. The device of PTL 3 constructs a three-dimensional person model using the generated silhouette image, and acquires the angle of each joint, the length between the joints, and the movement distance of the joint as parameters. The device of PTL 3 analyzes a gait state by comparing a parameter sequence cut out for each gait cycle calculated from a parameter with dictionary data indicating a motion during gait generated in advance. PTL 3 discloses that a parameter sequence of a healthy person is stored as dictionary data for each person attribute such as height, weight, age, and gender.

CITATION LIST

Patent Literature

PTL 1: US 2016/0100801 A
PTL 2: WO 2018/164157 A1
PTL 3: JP 2010-017447 A

SUMMARY OF INVENTION

Technical Problem

According to the method of PTL 1, it is possible to calculate intensity metrics such as pronation degree and pronation excursion based on the waveform feature of time series data of measurement values measured by a motion sensor. However, in the method of PTL 1, it is necessary for an expert to make a determination according to the calculated intensity metric.

According to the method of PTL 2, it is possible to determine whether there is an abnormality in the pronation foot/supination foot based on the data of the plantar pressure measured by the pressure sensor. Usually, it is not possible to obtain an accurate determination result regarding the presence or absence of abnormality in the pronation foot/supination foot unless it is determined according to attributes such as gender and age. In the method of PTL 2, since determination cannot be made according to attributes such as gender and age, an accurate determination result may not be obtained. In the method of PTL 2, since the determination is made based on the data of the plantar pressure measured by the pressure sensor, the feature appearing in the period of the swing phase cannot be extracted.

According to the method of PTL 3, since the dictionary data serving as the basis of the analysis is classified for each person attribute, the gait state can be analyzed according to the attribute of the pedestrian by comparing the parameter sequence with the dictionary data closer to the person attribute. However, in the method of PTL 3, it is necessary to use images captured from multiple directions in order to analyze the gait state. In the method of PTL 3, since analysis is performed based on the attribute of a healthy person, the degree of abnormality due to injury or disease cannot be verified.

An object of the present disclosure is to provide an estimation device and the like capable of estimating a physical condition according to an attribute based on sensor data measured along with gait.

Solution to Problem

An estimation device according to an aspect of the present disclosure includes a feature amount extraction unit that extracts, from a gait waveform extracted from time series data of sensor data based on a motion of a foot of a user, a feature amount according to an attribute of the user in a section in which a feature of a physical condition according to the attribute appears, and an inference unit that estimates the physical condition of the user using the feature amount extracted according to the attribute of the user.

In an estimation method according to an aspect of the present disclosure executed by a computer, the method includes extracting, from a gait waveform extracted from time series data of sensor data based on a motion of a foot of a user, a feature amount according to an attribute of the user in a section in which a feature of a physical condition according to the attribute appears, and estimating the physical condition of the user using the feature amount extracted according to the attribute of the user.

A program according to an aspect of the present disclosure causes a computer to execute a process of extracting, from a gait waveform extracted from time series data of sensor data based on a motion of a foot of a user, a feature amount according to an attribute of the user in a section in which a feature of a physical condition according to the attribute appears, and a process of estimating the physical condition of the user using the feature amount extracted according to the attribute of the user.

Advantageous Effects of Invention

According to the present disclosure, it is possible to provide an estimation device and the like capable of estimating a physical condition according to an attribute based on sensor data measured with gait.

BRIEF DESCRIPTION OF DRAWINGS

Figure 24:
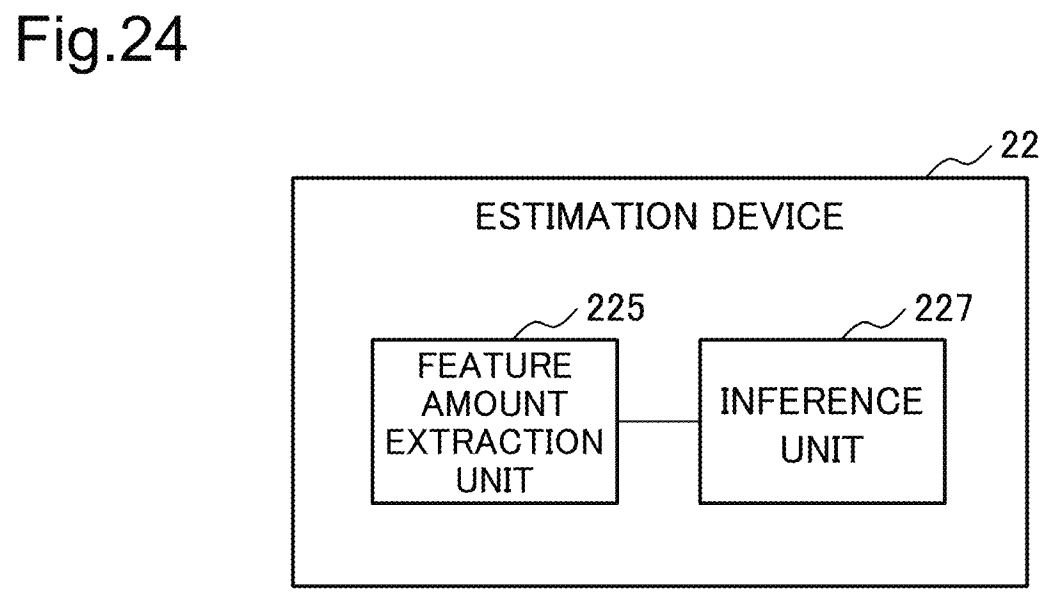

FIG. 24 is a block diagram illustrating an example of a configuration of an estimation device according to a second example embodiment.

FIG. 25 is a block diagram illustrating an example of a hardware configuration for achieving the estimation device according to each example embodiment.

EXAMPLE EMBODIMENT

Figure 1:
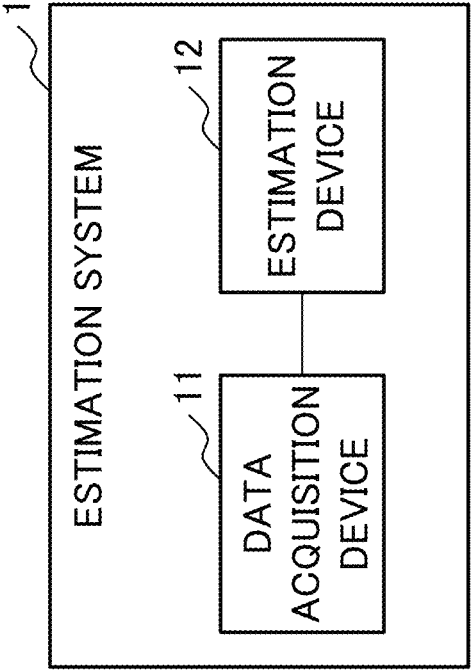
FIG. 1 is a block diagram illustrating an example of a configuration of an estimation system according to a first example embodiment.

Hereinafter, embodiments of the present invention will be described with reference to the drawings. However, the example embodiments described below have technically preferable limitations for carrying out the present invention, but the scope of the invention is not limited to the following. In all the drawings used in the following description of the example embodiment, the same reference numerals are given to the same parts unless there is a particular reason. In the following example embodiments, repeated description of similar configurations and operations may be omitted.

First Example Embodiment

An estimation system according to a first example embodiment of the present disclosure will be described with reference to the drawings. The estimation system of the present example embodiment measures a feature (also referred to as a gait) included in the gait pattern of the user, and analyzes the measured gait to estimate the physical condition of the user. In the present example embodiment, an example of estimating the degree of pronation/supination of the foot according to the attribute such as the gender and the age of the user based on the sensor data regarding the motion of the foot will be described. The physical condition estimated by the method of the present example embodiment is not limited to the degree of pronation/supination of the foot, and can also be used for estimation of a physical condition reflecting the influence of a difference in attributes such as gender and age, such as hallux valgus, leg O/leg X, and the degree of obesity. In the present example embodiment, a system in which the right foot is a reference foot and the left foot is an opposite foot will be described. The method of the present example embodiment can also be applied to a system in which the left foot is a reference foot and the right foot is an opposite foot.

(Configuration)

FIG. 1 is a block diagram illustrating a configuration of an estimation system 1 of the present example embodiment. The estimation system 1 includes a data acquisition device 11 and an estimation device 12. The data acquisition device 11 and the estimation device 12 may be connected by wire or wirelessly. The data acquisition device 11 and the estimation device 12 may be configured by a single device. Alternatively, the data acquisition device 11 may be excluded from the configuration of the estimation system 1, and only the estimation device 12 may constitute the estimation system 1.

The data acquisition device 11 is installed at a foot portion. For example, the data acquisition device 11 is installed at footwear such as a shoe. In the present example embodiment, an example in which the data acquisition device 11 is disposed at a position on the back side of the arch of the foot will be described. The data acquisition device 11 includes an acceleration sensor and an angular velocity sensor. Data acquisition device 11 measures a physical quantity such as an acceleration (also referred to as a spatial acceleration) measured by an acceleration sensor and an angular velocity (also referred to as a spatial angular velocity) measured by an angular velocity sensor as a physical quantity regarding the motion of the foot of the user wearing the footwear. The physical quantities regarding the motion of the foot measured by the data acquisition device 11 also include a speed, an angle, and a position (trajectory) calculated by integrating acceleration and angular velocity. The data acquisition device 11 converts the measured physical quantity into digital data (also referred to as sensor data). The data acquisition device 11 transmits the converted sensor data to the estimation device 12. For example, the data acquisition device 11 is connected to the estimation device 12 via a mobile terminal (not illustrated) carried by the user.

The mobile terminal (not illustrated) is a communication device that can be carried by a user. For example, the mobile terminal is a portable communication device having a communication function, such as a smartphone, a smart watch, or a mobile phone. The mobile terminal receives, from the data acquisition device 11, sensor data regarding the motion of the user's foot. The mobile terminal transmits the received sensor data to a server or the like on which the estimation device 12 is mounted. The function of the estimation device 12 may be implemented by application software or the like installed in the mobile terminal. In this case, the mobile terminal processes the received sensor data by application software or the like installed therein.

The data acquisition device 11 is achieved by, for example, an inertial measurement device including an acceleration sensor and an angular velocity sensor. An example of the inertial measurement device is an inertial measurement unit (IMU). The IMU includes the acceleration sensor that measures acceleration in the three axial directions and the angular velocity sensor that measures angular velocities around the three axes. The data acquisition device 11 may be achieved by an inertial measurement device such as a vertical gyro (VG) or an attitude heading (AHRS). The data acquisition device 11 may be achieved by a global positioning system/inertial navigation system (GPS/INS).

Figure 2:
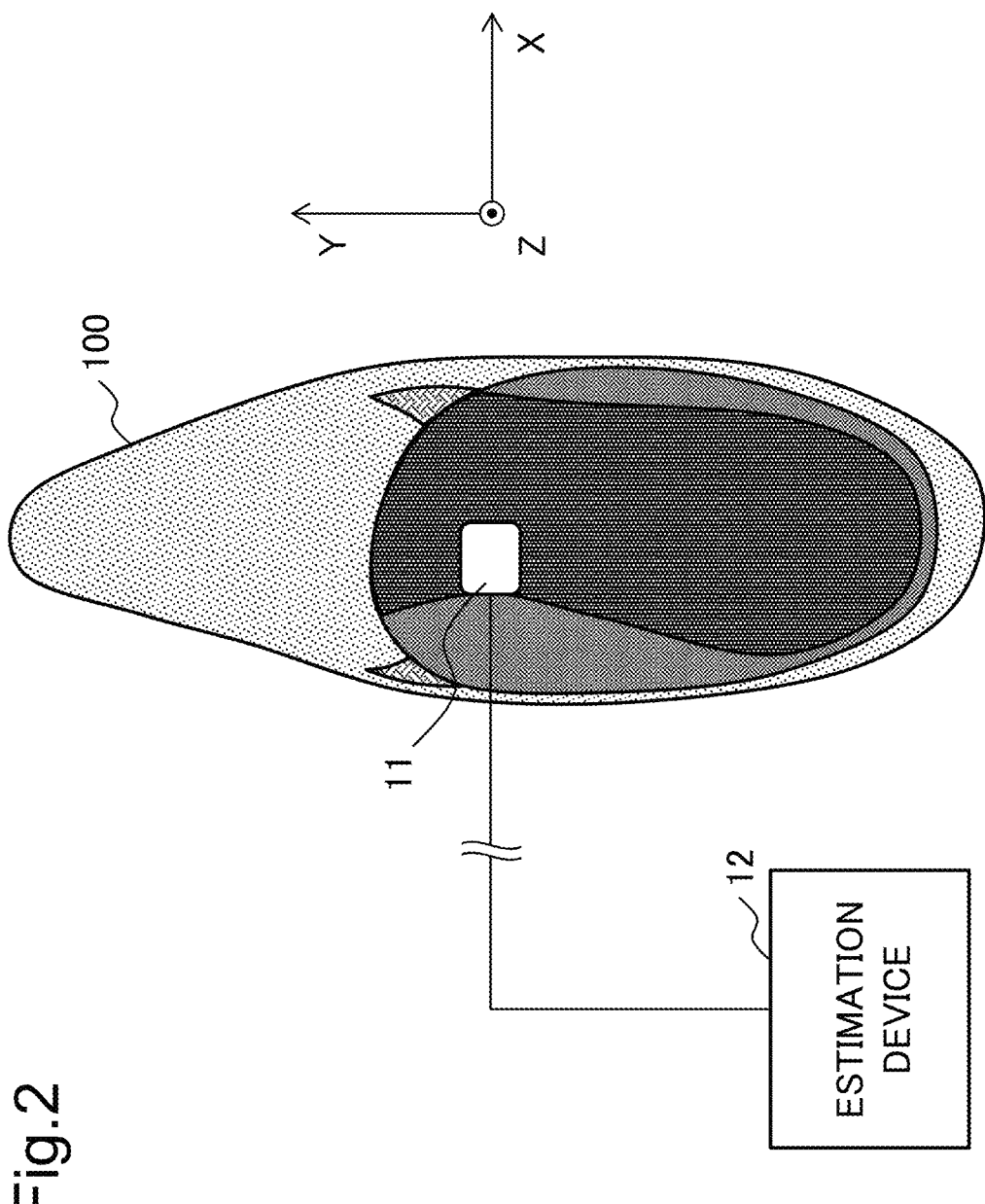
FIG. 2 is a conceptual diagram illustrating an example in which a data acquisition device of the estimation system according to the first example embodiment is disposed in footwear.

FIG. 2 is a conceptual diagram illustrating an example in which the data acquisition device 11 is disposed in the shoe 100. In the example of FIG. 2, the data acquisition device 11 is installed in an arrangement related to the back side of the arch of the foot. For example, the data acquisition device 11 is disposed in an insole inserted into the shoe 100. For example, the data acquisition device 11 is disposed on the bottom face of the shoe 100. For example, the data acquisition device 11 is embedded in the main body of the shoe 100. The data acquisition device 11 may be detachable from the shoe 100 or may not be detachable from the shoe 100. The data acquisition device 11 may be installed at a position not related to the back side of the arch of the foot as long as it can acquire sensor data regarding the motion of the foot. The data acquisition device 11 may be installed on a sock worn by the user or a decorative article such as an anklet worn by the user. The data acquisition device 11 may be directly attached to the foot or may be embedded in the foot. FIG. 2 illustrates an example in which the data acquisition device 11 is installed in the shoe 100 on the right foot side, but the data acquisition device 11 may be installed in the shoe 100 for both feet. When the data acquisition device 11 is installed in the shoe 100 for both feet, the physical condition can be estimated based on the motion of the legs/feet.

Figure 3:
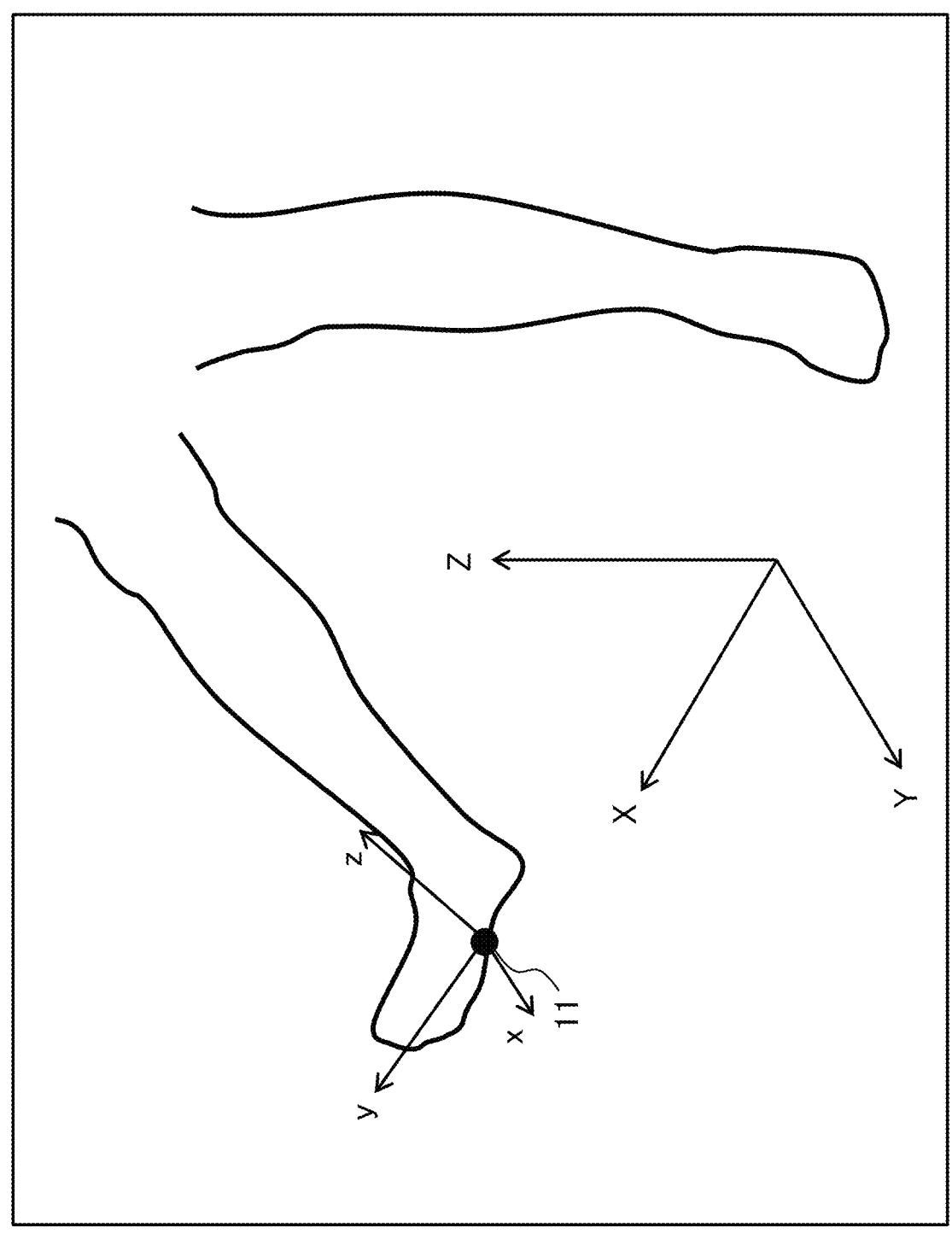
FIG. 3 is a conceptual diagram for describing a relationship between a local coordinate system and a world coordinate system set in the data acquisition device of the estimation system according to the first example embodiment.

FIG. 3 is a conceptual diagram for explaining a local coordinate system (x-axis, y-axis, z-axis) set in the data acquisition device 11 and a world coordinate system (X-axis, Y-axis, Z-axis) set with respect to the ground in a case where the data acquisition device 11 is installed at a position of the back side of the arch of the foot. In the world coordinate system (X-axis, Y-axis, Z-axis), in a state where the user is standing upright, a lateral direction of the user is set to an X-axis direction (rightward direction is positive), a front direction of the user (traveling direction) is set to a Y-axis direction (forward direction is positive), and a gravity direction is set to a Z-axis direction (vertically upward direction is positive). In the present example embodiment, a local coordinate system including the x direction, the y direction, and the z direction based on the data acquisition device 11 is set.

Figure 4:
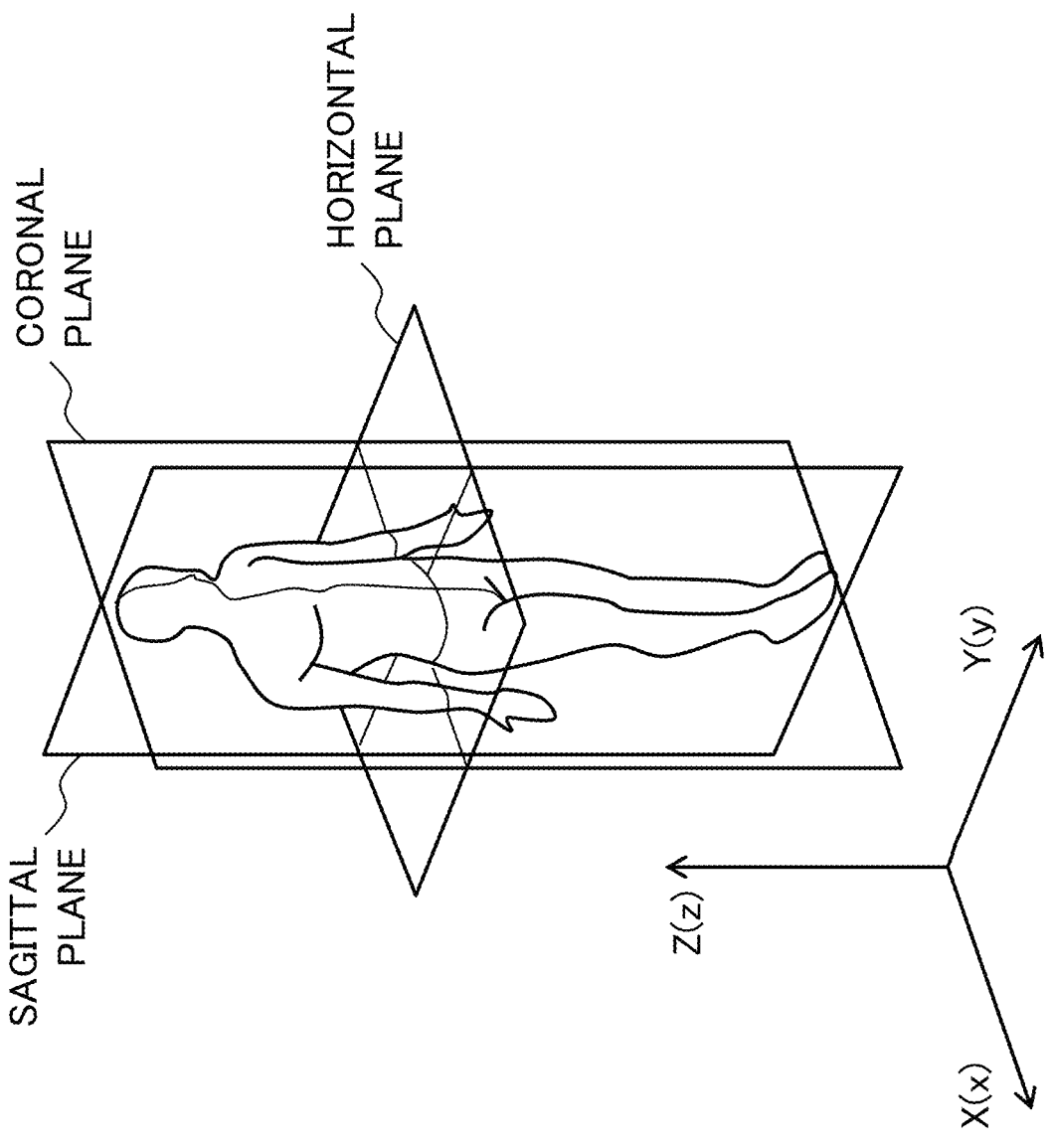
FIG. 4 is a conceptual diagram for explaining a human body surface.

FIG. 4 is a conceptual diagram for explaining a face (also referred to as a human body surface) set for the human body. In the present example embodiment, a sagittal plane dividing the body into left and right, a coronal plane dividing the body into front and rear, and a horizontal plane dividing the body horizontally are defined. In the upright state as illustrated in FIG. 4, the world coordinate system coincides with the local coordinate system. In the present example embodiment, rotation in the sagittal plane with the x-axis as a rotation axis is defined as roll, rotation in the coronal plane with the Y-axis as a rotation axis is defined as pitch, and rotation in the horizontal plane with the Z-axis as a rotation axis is defined as yaw. A rotation angle in a sagittal plane with the x-axis as a rotation axis is defined as a roll angle, a rotation angle in a coronal plane with the y-axis as a rotation axis is defined as a pitch angle, and a rotation angle in a horizontal plane with the z-axis as a rotation axis is defined as a yaw angle. In the present example embodiment, an example in which the degree of pronation/supination of the foot is determined based on the pitch angle will be described. In the present example embodiment, the pitch angle is set in such a way that rotation in the abduction direction (counterclockwise rotation about the y-axis) is positive, and rotation in the adduction direction (clockwise rotation about the y-axis) is negative.

Figure 5:
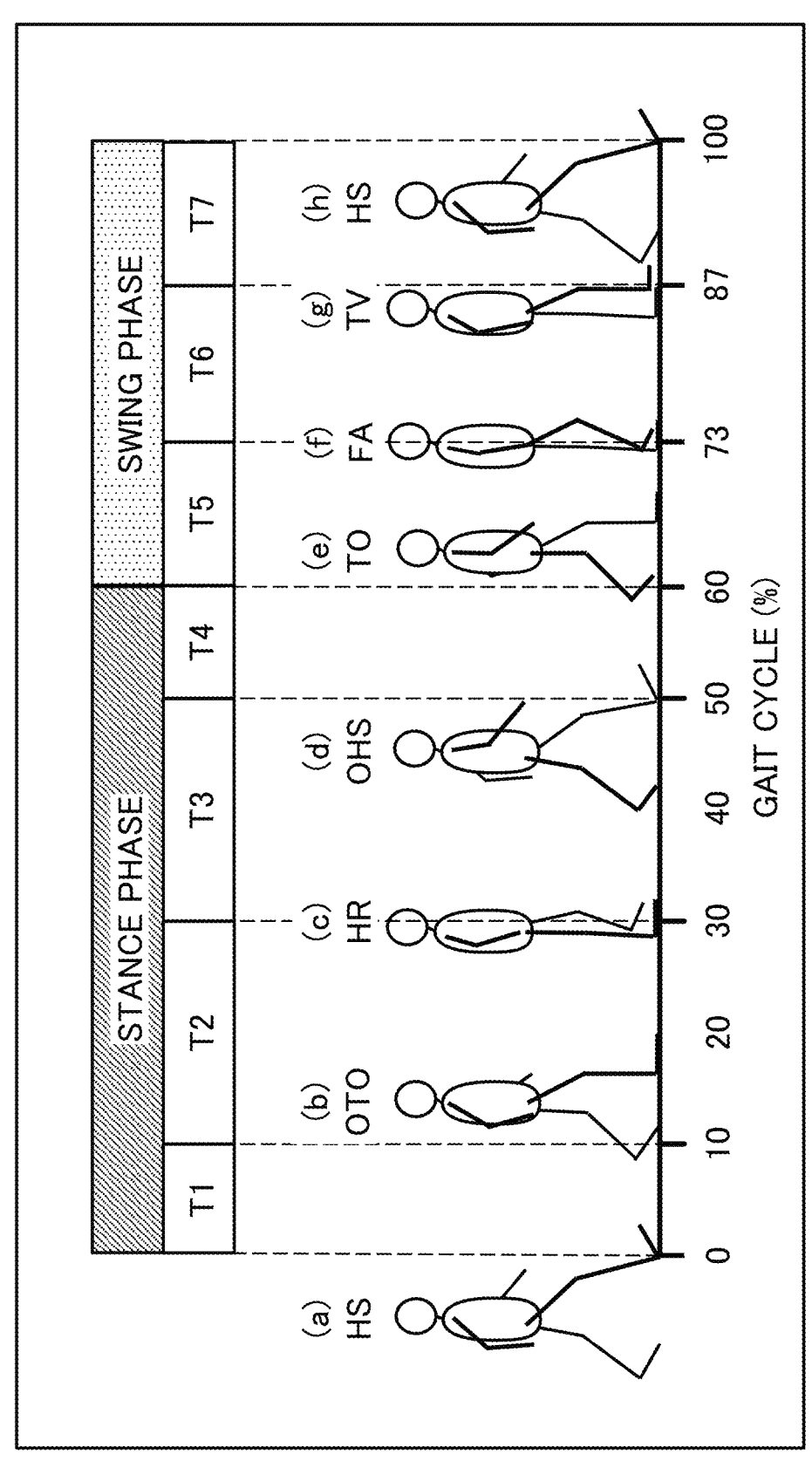
FIG. 5 is a conceptual diagram for explaining a gait event.

FIG. 5 is a conceptual diagram for explaining one gait cycle with the right foot as a reference. The horizontal axis of FIG. 5 is a normalized gait cycle with one gait cycle of the right foot as 100% with a time point at which the heel of the right foot lands on the ground as a starting point and a time point at which the heel of the right foot lands on the ground next as an ending point. The one gait cycle of one foot is roughly divided into a stance phase in which at least part of the back side of the foot is in contact with the ground and a swing phase in which the back side of the foot is away from the ground. In the present example embodiment, normalization is performed in such a way that the stance phase occupies 60% and the swing phase occupies 40%. The stance phase is further subdivided into an initial stance period T1, a mid-stance period T2 of standing, a terminal stance period T3 of standing, and a pre-swing period T4. The swing phase is further subdivided into an initial swing period T5, a mid-swing period T6, and a terminal swing period T7. In the gait waveform for one gait cycle, the time point when the heel lands on the ground may not be set as a starting point.

FIG. 5($a$) represents an event (heel strike (HS)) in which the heel of the right foot is grounded. FIG. 5($b$) illustrates an event (opposite toe off (OTO)) in which the toe of the left foot moves away from the ground while the ground contact surface of the sole of the right foot is in contact with the ground. FIG. 5($c$) illustrates an event (heel rise (HR)) in which the heel of the right foot is lifted while the ground contact surface of the sole of the right foot is in contact with the ground. FIG. 5($d$) is an event (opposite heel strike (OHS)) in which the heel of the left foot is grounded. FIG. 5($e$) illustrates an event (toe off (TO)) in which the toe of the right foot is separated from the ground while the ground contact surface of the sole of the left foot is in contact with the ground. FIG. 5($f$) illustrates an event (foot adjacent (FA)) in which the left foot and the right foot intersect with each other in a state where the ground contact surface of the sole of the left foot is grounded. FIG. 5($g$) illustrates an event (tibia vertical (TV)) in which the tibia of the left foot is substantially perpendicular to the ground while the sole of the right foot is grounded. FIG. 5($h$) represents an event (heel strike (HS)) in which the heel of the right foot is grounded. FIG. 5($h$) corresponds to the ending point of the gait cycle starting from FIG. 5($a$) and corresponds to the starting point of the next gait cycle.

Figure 6:
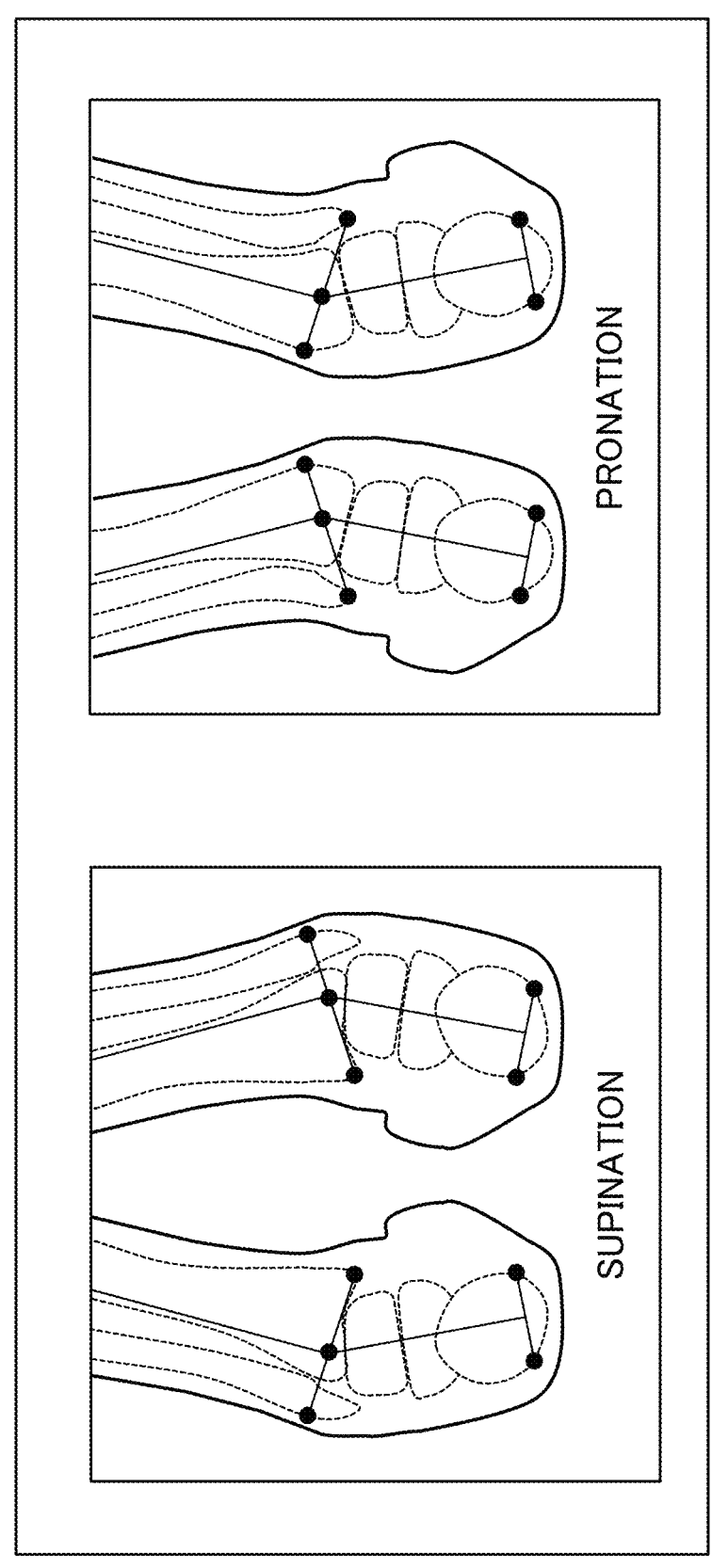
FIG. 6 is a conceptual diagram for explaining pronation/supination of a foot.

Next, the pronation/supination of the foot will be described with reference to the drawings. FIG. 6 is a conceptual diagram for explaining pronation/supination of the foot. Pronation/supination of the foot is a triplanar motion that simultaneously includes motions in the coronal plane, sagittal plane and horizontal plane. In the present example embodiment, pronation/supination of the foot is regarded as coronal plane movement of the subtalar joint. In the present example embodiment, since the angle in the coronal plane when the person is standing upright is used, the sensor data in the local coordinate system is converted into the world coordinate system when calculating the pitch angle. The supination is a movement in which the foot portion is configured by adduction, plantarflexion, and inversion. The pronation is a motion including eversion, dorsiflexion, and eversion. For example, a foot having a large degree of pronation and fixed in this state is referred to as a pronation foot. Similarly, a foot having a large degree of supination and fixed in this state is referred to as a supination foot.

Figure 7:
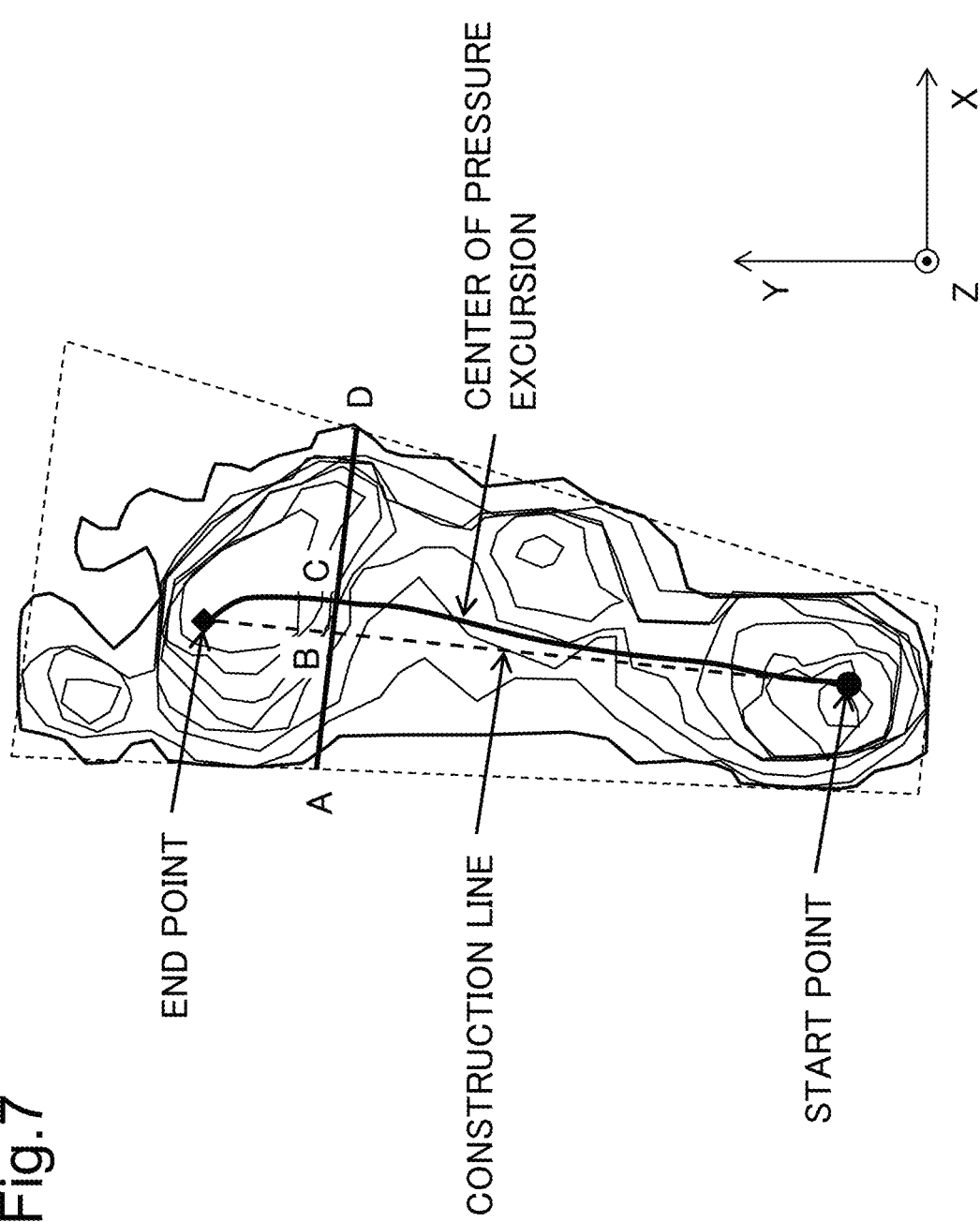
FIG. 7 is a conceptual diagram for explaining a center of pressure excursion index (CPEI) derived from a foot pressure distribution.

The degree of pronation/supination of the foot can be evaluated by the center of pressure excursion index (CPEI). FIG. 7 is a conceptual diagram for explaining CPEI. FIG. 7 illustrates a center of pressure (CoP) trajectory superimposed on the foot pressure distribution. The center of pressure excursion is a trajectory obtained by connecting the maximum points (maximum load center) of the foot pressure on a line obtained by cutting the foot pressure distribution in the floor surface (in the XY plane) along the coronal plane (ZX plane) from the heel strike point (start point) to the toe off (end point) along the Y-axis direction. A straight line connecting a start point and an end point is referred to as a construction line. A trapezoid whose base is perpendicular to the construction line surrounds the contour of the foot, and is cut along a cutting line parallel to the base of the trapezoid at the $\frac{1}{3}$ distance of the length of the foot away from a front position of the foot in the length direction. Among intersections of the trapezoid and the cutting line, an inner point of the foot is A, and an outer point of the foot is D. An intersection of the construction line and the cutting line is defined as B, and an intersection of the center of pressure excursion and the cutting line is defined as C. The line segment BC is referred to as a center of pressure excursion (CPE). The line segment AD corresponds to a foot width. As shown in the following Expression 1, the ratio of the CPE (the length of the line segment BC) to the foot width (the length of the line segment AD) corresponds to the center of pressure excursion index CPEI (Expression 1).

$$CPEI = CPE/\text{Foot width} \times 100 \qquad (1)$$

However, the start point and the end point, the manner of surrounding with the trapezoid, the manner of cutting the trapezoid, and the like used to derive the CPEI are merely examples, and the CPEI is not limited to the above definition.

Figure 8:
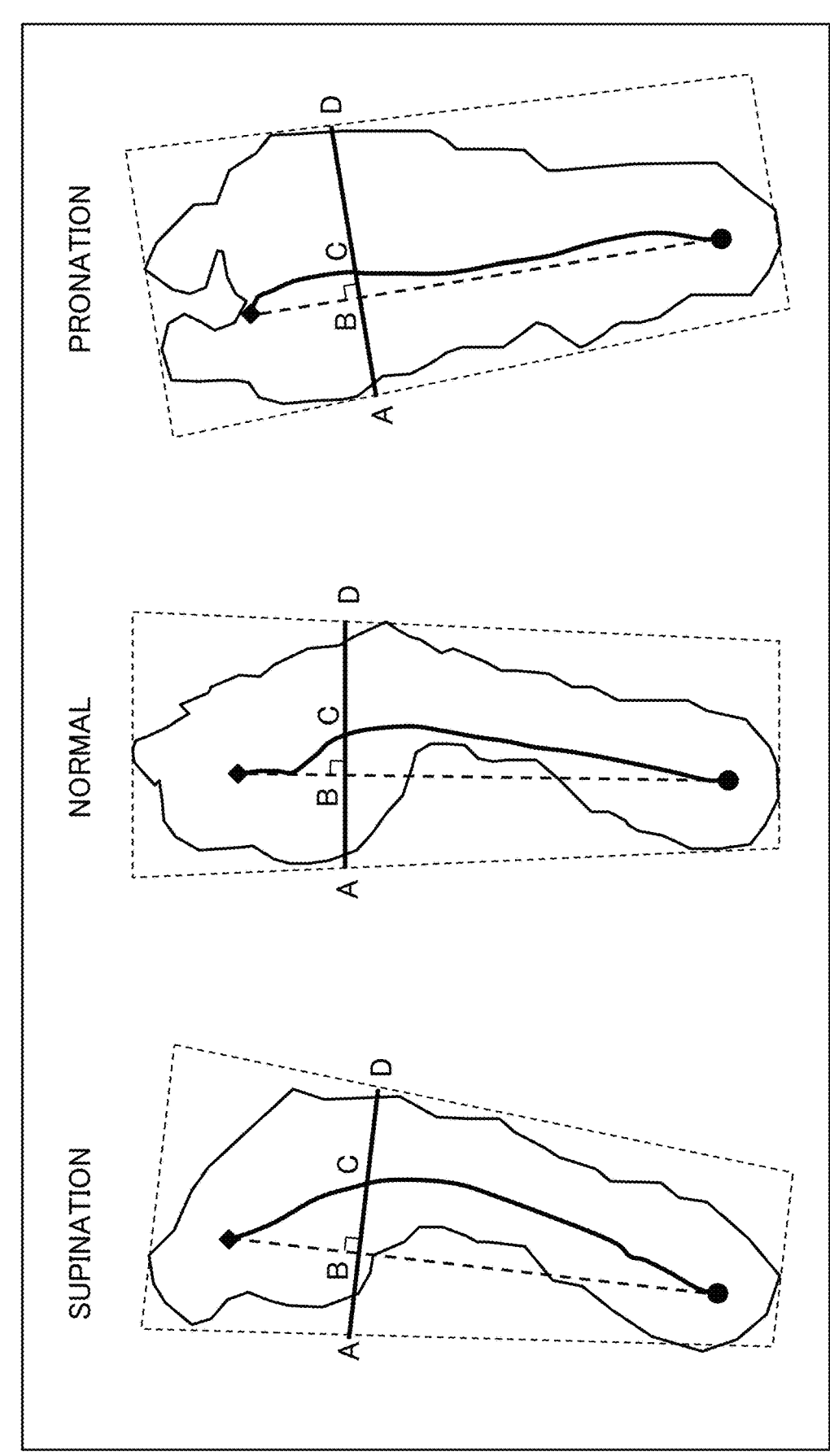
FIG. 8 is a conceptual diagram for explaining a difference in CPEI depending on the degree of pronation/supination of the foot.

FIG. 8 is a conceptual diagram for comparing CPEI for a foot that has a tendency of supination, normal, and pronate. In the case of supination, the CPE (length of the line segment BC) tends to be longer and the foot width (length of the line segment AD) tends to be smaller than those in the normal state. On the other hand, in the case of pronation, the CPE (length of the line segment BC) tends to be shorter and the foot width (length of the line segment AD) tends to be larger than those in the normal state. That is, it can be determined that a state in which the CPEI is excessively large is supination and a state in which the CPEI is excessively small is pronation. In the present example embodiment, when the CPEI is equal to or more than 20, it is classified into supination, when the CPEI is 9 to 20, it is classified into normal classification, and when the CPEI is equal to or less than 9, it is classified into pronation. The determination criterion based on the value of CPEI is an example of the degree of pronation/supination of the foot, and the determination criterion of the degree of pronation/supination of the foot is not limited as described above.

The estimation device 12 acquires sensor data regarding the motion of the foot of the user. The degree of pronation/supination of the foot correlates with the adduction angle/abduction angle. The estimation device 12 estimates the degree of pronation/supination of the foot using a waveform (also referred to as a gait waveform) based on time series data of the acquired sensor data based on a standard according to an attribute such as gender and age. In the present example embodiment, the estimation device 12 estimates the degree of pronation/supination of the foot using a gait waveform of a rotation angle (also referred to as a pitch angle) of the foot in the coronal plane (zx plane). In other words, the estimation device 12 estimates the degree of pronation/supination of the foot using the time series data of the pitch angle which is the rotation angle of the foot around the Y-axis. Specifically, the estimation device 12 estimates the degree of pronation/supination of the foot using the feature amount extracted from the pitch angle time series data based on the standard according to the attribute. When the physical condition different from the degree of pronation/supination of the foot is estimated, a gait waveform in which the feature of the physical condition appears may be used. For example, the estimation device 12 estimates the degree of pronation/supination of the foot using an inference model generated for each attribute. The inference model for each attribute will be described later.

Figure 9:
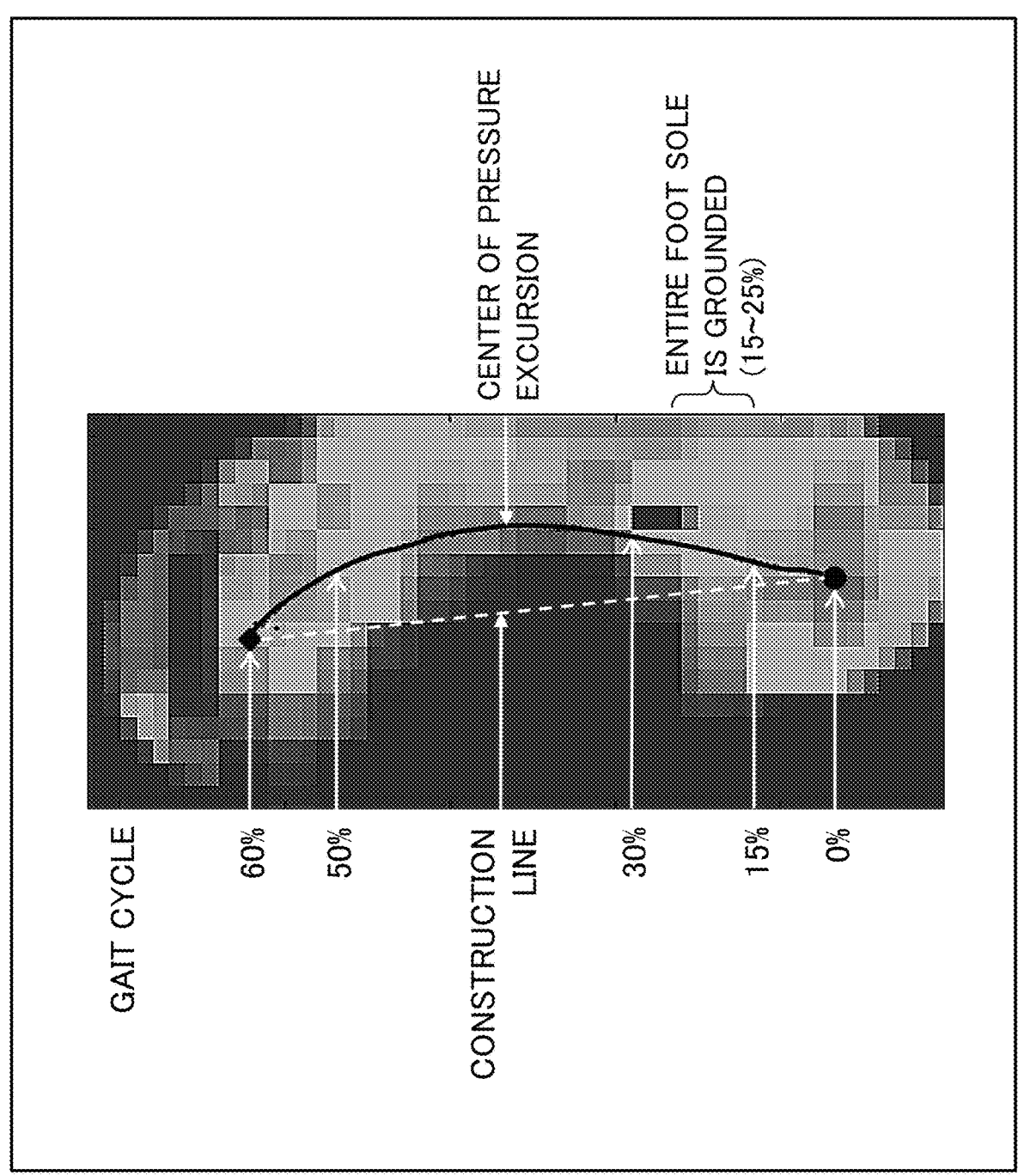
FIG. 9 is a conceptual diagram for explaining an example of a correspondence relationship between a center of pressure excursion and a gait cycle.

FIG. 9 is a conceptual diagram for describing a correspondence relationship between the center of pressure excursion and the gait cycle. FIG. 9 illustrates a foot pressure distribution measured for a certain subject, and a construction line and a center of pressure excursion in the foot pressure distribution. On the left side of the foot pressure distribution, the gait cycle related to the center of pressure excursion is shown. 15 to 25% of the gait cycle is a state in which the sole of the right foot is entirely in contact with the ground (foot flat). The sole full ground contact means that the entire ground contact surface of the sole is grounded. In a state of the sole full ground contact (foot flat), the pitch angle is 0 degrees. 30% of the gait cycle corresponds to the timing of heel rise. Over 30 to 50% of the gait cycle, the area of the sole contacting the ground gradually decreases as the weight moves from the heel to the toe of the right foot. 60% of the gait cycle is the timing of toe off at which the toe of the right foot leaves the ground.

When the foot has a tendency to supination, the curve of the CPEI is steep because the contact portion between the sole and the ground is biased to the outer side of the foot. In this case, there is a tendency of adduction, and the pitch angle decreases at the terminal stance period which is 30 to 50% of the gait cycle. When the degree of supination is excessive, the pitch angle may be negative. On the other hand, when there is a tendency of pronation, the contact portion between the sole and the ground is biased to the inner side of the foot, so that the curve of the CPEI is loose. In this case, there is a tendency of eversion, and the pitch angle increases at the terminal stance period which is 30 to 50% of the gait cycle.

The inventors of the present disclosure have found that the feature amount that can be used to estimate the degree of pronation/supination of the foot appears in a different gait cycle (also referred to as a gait phase) according to attributes such as gender and age.

For example, in the case of a male, a feature amount applicable to the estimation of the degree of pronation/supination of the foot appears in the latter half of the stance phase (immediately before toe off) and the latter half of the swing phase (immediately before heel strike). For example, in the case of a female, a feature amount applicable to the estimation of the degree of pronation/supination of the foot appears in the first half of the stance phase (immediately after heel strike and a period of single-leg support). Therefore, in a case where gender is used as the attribute, features extracted from the latter half of the stance phase, the latter half of the swing phase (male), and the first half of the stance phase (female) may be used.

For example, in the case of the young of about 20 to 39 years of age, a feature amount applicable to the estimation of the degree of pronation/supination of the foot appears in the latter half of the stance phase (immediately before toe off) and the latter half of the swing phase (immediately before heel strike). For example, in the case of the elderly of 60 years of age or older, a feature amount applicable to the estimation of the degree of pronation/supination of the foot appears in the first half of the stance phase (immediately after heel strike) and the latter half of the swing phase (immediately before heel strike). In a case where age is used as the attribute, in the latter half of the swing phase (immediately before heel strike), the gait phases in which the features appear between the young and the elderly are close. Therefore, in a case where age is used as the attribute, features extracted from the latter half of the stance phase (the young) and the first half of the stance phase (the elderly) in which the gait phases in which the features appear are different between the young and the elderly may be used.

For example, the estimation device 12 is implemented by a server (not illustrated) or the like. For example, the estimation device 12 may be implemented by an application server. For example, the estimation device 12 may be implemented by application software or the like installed in a mobile terminal (not illustrated).

[Data Acquisition Device]

Figure 10:
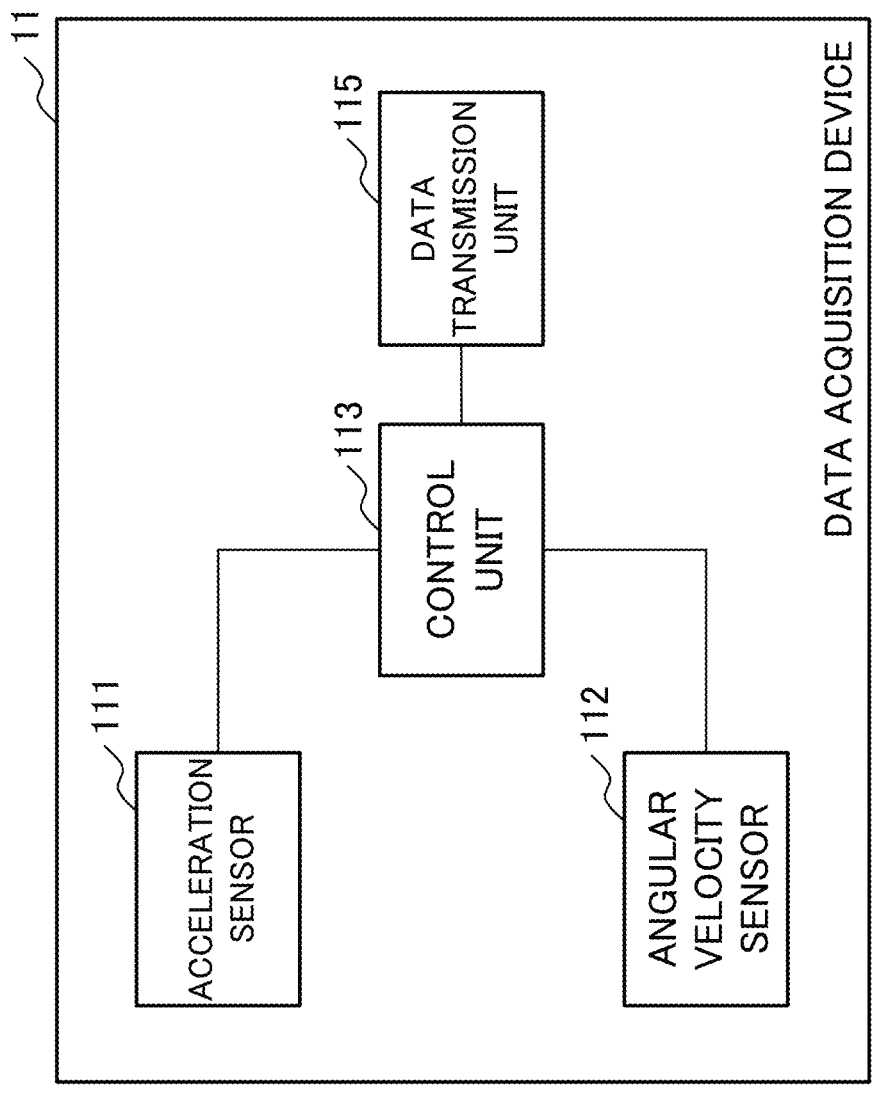
FIG. 10 is a block diagram illustrating an example of a configuration of the data acquisition device of the estimation system according to the first example embodiment.

Next, a detailed configuration of the data acquisition device 11 will be described with reference to the drawings. FIG. 10 is a block diagram illustrating an example of a detailed configuration of the data acquisition device 11. The data acquisition device 11 includes an acceleration sensor 111, an angular velocity sensor 112, a control unit 113, and a data transmission unit 115. The data acquisition device 11 includes a power supply (not illustrated).

The acceleration sensor 111 is a sensor that measures acceleration (also referred to as spatial acceleration) in the three axial directions. The acceleration sensor 111 outputs the measured acceleration to the control unit 113. For example, a sensor of a piezoelectric type, a piezoresistive type, a capacitance type, or the like can be used as the acceleration sensor 111. As long as the sensor used for the acceleration sensor 111 can measure acceleration, the measurement method is not limited.

The angular velocity sensor 112 is a sensor that measures angular velocities in three axial directions (also referred to as spatial angular velocities). Angular velocity sensor 112 outputs the measured angular velocity to control unit 113. For example, a sensor of a vibration type, a capacitance type, or the like can be used as the angular velocity sensor 112. As long as the sensor used for the angular velocity sensor 112 can measure an angular velocity, the measurement method is not limited.

The control unit 113 acquires the acceleration in the three axial directions and the angular velocity around the three axes from each of the acceleration sensor 111 and the angular velocity sensor 112. The control unit 113 converts the acquired acceleration and angular velocity into digital data to output the converted digital data (also referred to as sensor data) to the data transmission unit 115. The sensor data includes at least acceleration data converted into digital data and angular velocity data converted into digital data. The acceleration data includes acceleration vectors in three axial directions. The angular velocity data includes angular velocity vectors around the three axes. The acquisition times of the acceleration data and the angular velocity data are associated with the acceleration data and the angular velocity data. The control unit 113 may be configured to output sensor data obtained by adding correction such as a mounting error, temperature correction, and linearity correction to the acquired acceleration data and angular velocity data. The control unit 113 may generate angle data around the three axes using the acquired acceleration data and angular velocity data.

For example, the control unit 113 is a microcomputer or a microcontroller that performs overall control and data processing of the data acquisition device 11. For example, the control unit 113 includes a central processing unit (CPU), a random access memory (RAM), a read only memory (ROM), a flash memory, and the like. The control unit 113 controls the acceleration sensor 111 and the angular velocity sensor 112 to measure the angular velocity and the acceleration. For example, the control unit 113 performs analog-to-digital conversion (AD conversion) on physical quantities (analog data) such as the measured angular velocity and acceleration, and stores the converted digital data in the flash memory. The physical quantity (analog data) measured by each of the acceleration sensor 111 and the angular velocity sensor 112 may be converted into digital data in each of the acceleration sensor 111 and the angular velocity sensor 112. The digital data stored in the flash memory is output to the data transmission unit 115 at a predetermined timing.

The data transmission unit 115 acquires sensor data from the control unit 113. The data transmission unit 115 transmits the acquired sensor data to the estimation device 12. The data transmission unit 115 may transmit the sensor data to the estimation device 12 via a wire such as a cable, or may transmit the sensor data to the estimation device 12 via wireless communication. For example, the data transmission unit 115 is configured to transmit sensor data to the estimation device 12 via a wireless communication function (not illustrated) conforming to a standard such as Bluetooth (registered trademark) or WiFi (registered trademark). The communication function of the data transmission unit 115 may conform to a standard other than Bluetooth (registered trademark) or WiFi (registered trademark).

[Estimation Device]

Figure 11:
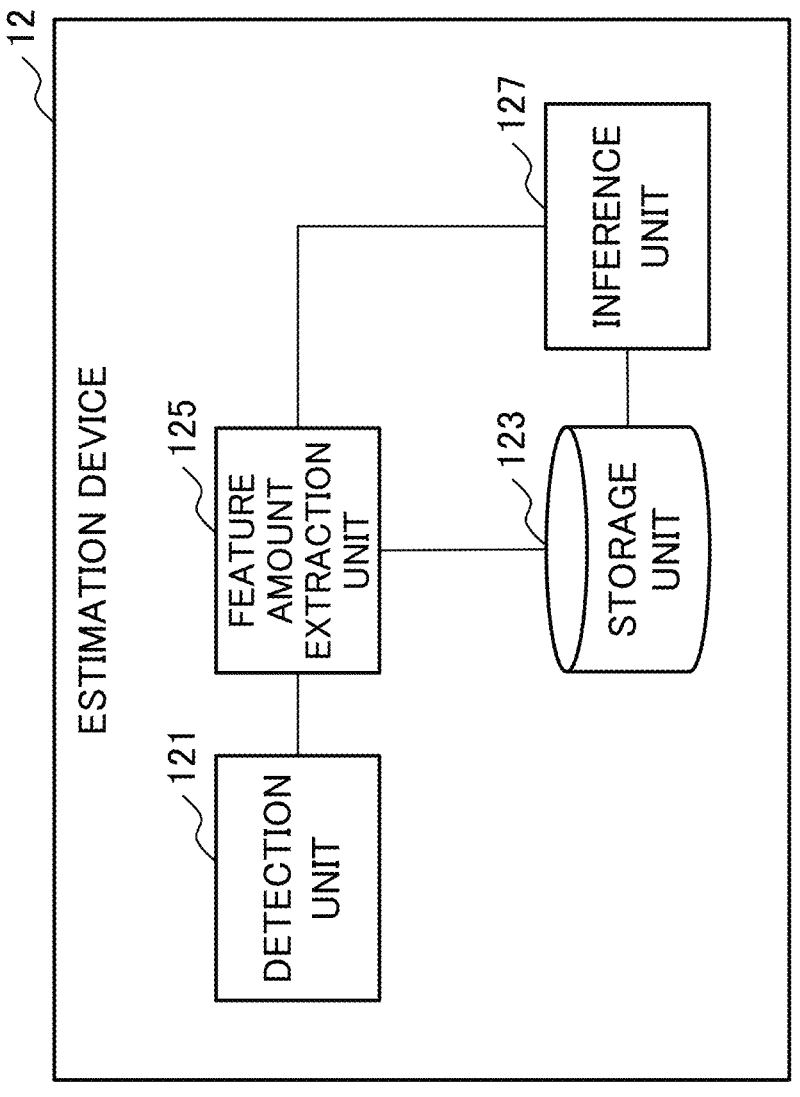
FIG. 11 is a block diagram illustrating an example of a configuration of an estimation device of an estimation system according to the first example embodiment.

Next, a detailed configuration of the estimation device 12 included in the estimation system 1 will be described with reference to the drawings. FIG. 11 is a block diagram illustrating an example of a configuration of the estimation device 12. The estimation device 12 includes a detection unit 121, a feature amount extraction unit 125, a storage unit 123, and an inference unit 127. In practice, a communication interface such as a reception unit that receives sensor data from the data acquisition device 11 and an output unit that outputs an inference result by the inference unit 127 is provided. In the present example embodiment, the communication interface is omitted.

The detection unit 121 acquires sensor data from the data acquisition device 11. For example, the detection unit 121 converts the coordinate system of the acquired sensor data from the local coordinate system to the world coordinate system. When the user is standing upright, the local coordinate system (x-axis, y-axis, z-axis) coincides with the world coordinate system (X-axis, Y-axis, Z-axis). Since the spatial posture of the data acquisition device 11 changes while the user is walking, the local coordinate system (x-axis, y-axis, z-axis) do not coincide with the world coordinate system (X-axis, Y-axis, Z-axis). Therefore, the detection unit 121 converts the sensor data acquired by the data acquisition device 11 from the local coordinate system (x-axis, y-axis, z-axis) of the data acquisition device 11 into the world coordinate system (X-axis, Y-axis, Z-axis).

Using the sensor data, the detection unit 121 generates time series data of a physical quantity regarding the motion of the foot measured along with gait of the pedestrian wearing the footwear at which the data acquisition device 11 is installed. For example, the detection unit 121 generates time series data such as a spatial acceleration and a spatial angular velocity. The detection unit 121 integrates the spatial acceleration and the spatial angular velocity to generate time series data such as the spatial velocity, the spatial angle (plantar angle), and the spatial trajectory. These time series data correspond to the gait waveform. The detection unit 121 generates time series data at a predetermined timing or time interval set in accordance with a general gait cycle or a gait cycle unique to the user. The timing at which the detection unit 121 generates the time series data can be set at any timing. For example, the detection unit 121 is configured to continue to generate time series data during a period in which a gait of the user is continued. The detection unit 121 may be configured to generate time series data at a specific timing.

The detection unit 121 extracts time series data (also referred to as a gait waveform) for one gait cycle from the generated time series data. In the following description, an example in which a gait waveform in one gait cycle has a timing of heel strike as a starting point and a timing of next heel strike as an ending point will be described. For example, the detection unit 121 extracts a gait waveform of the acceleration in the traveling direction for one gait cycle from the time series data of the acceleration in the traveling direction (Y direction). For example, the detection unit 121 detects the timing of the toe off in the gait waveform of the acceleration in the traveling direction for one gait cycle. For example, the timing of the toe off is a timing at which a valley is detected between two peaks included in the maximum peak in the gait waveform of the acceleration in the traveling direction for one gait cycle. For example, the detection unit 121 detects the timing of the heel strike in the acceleration gait waveform in the traveling direction for one gait cycle. For example, the timing of the heel strike is a timing of the midpoint between the timing at which the minimum peak is detected and the timing at which the maximum peak appearing next to the minimum peak is detected in the acceleration gait waveform in the traveling direction for one gait cycle.

The storage unit 123 stores an inference model for each attribute generated in advance. The storage unit 123 stores an inference model for inferring the physical condition for each attribute such as gender and age.

Figure 12:
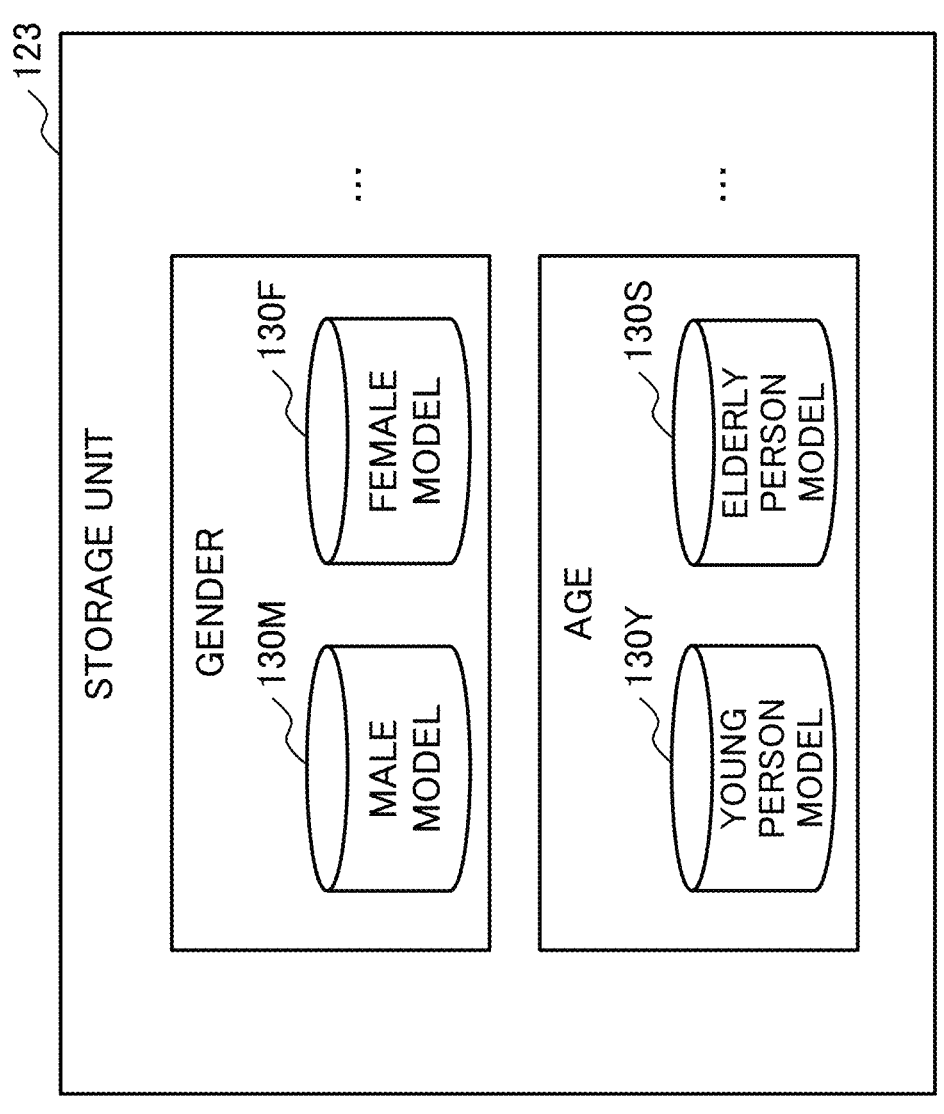
FIG. 12 is a conceptual diagram for explaining an example of an inference model for each attribute used by the estimation device of the estimation system according to the first example embodiment.

FIG. 12 is a conceptual diagram illustrating an example of an inference model 130 stored in the storage unit 123. The storage unit 123 stores the inference model 130, for each attribute, that estimates the physical condition according to the input of the feature amount extracted from the gait phase in which the difference due to the attribute such as the gender or the age appears. A male model 130M (also referred to as a male inference model) is a model for estimating the physical condition of a male. A female model 130F (also referred to as a female inference model) is a model for estimating the physical condition of a female. A young person model 130Y (also referred to as a young person inference model) is a model for estimating the physical condition of the young of about 20 to 39 years old. An elderly person model 130S (also referred to as an elderly person inference model) is a model for estimating the physical condition of the elderly of 60 years old or more. In a case where the attribute of the user is known in advance, the inference model 130 according to the attribute of the user may be stored in the storage unit 123.

An example of the gait cycle (gait phase) in which the feature amount input to each of the inference models 130 for each attribute is extracted in a case where the physical condition of the estimation target is the degree of pronation/ supination will be described. For example, the feature amount peculiar to the male is extracted from a period (also referred to as a male feature amount extraction period) including the latter half of the stance phase (immediately before toe off) and the latter half of the swing phase (immediately before heel strike) in the gait waveform of the pitch angle (also referred to as an angle waveform in the coronal plane). For example, the feature amount peculiar to a woman is extracted from a period (also referred to as a female feature amount extraction period) including the first half of the stance phase (a period immediately after heel strike and a period of single-leg support). For example, the feature amount peculiar to the young of about 20 to 39 years of age is extracted from a period (also referred to as a young person feature amount extraction period) including the latter half of the stance phase (immediately before toe off) and the latter half of the swing phase (immediately before heel strike). For example, the feature amount peculiar to the elderly of 60 years of age or older is extracted from a period (also referred to as the elderly person feature amount extraction period) including the first half of the stance phase (immediately after heel strike) and the latter half of the swing phase (immediately before heel strike). In a case where age is used as the attribute, in the latter half of the swing phase (immediately before heel strike), there is a tendency that the gait phases in which the features appear in the young and the elderly overlap. Therefore, in a case where age is used as the attribute, features extracted from the latter half of the stance phase (the young) and the first half of the stance phase (the elderly) in which the gait phases in which the features appear are different between the young and the elderly may be used.

The inference model 130 for each attribute outputs the estimation result regarding the physical condition according to the input of the feature amount of the pitch angle in the gait cycle (gait phase) according to the attribute. For example, the inference model 130 for each attribute outputs the estimation result regarding the degree of pronation/ supination of the foot according to the input of the feature amount of the pitch angle in the gait cycle (gait phase) according to the attribute. For example, the inference model 130 outputs the determination result of pronation/supination/normal of the foot as the estimation result regarding the degree of pronation/supination of the foot according to the input of the feature amount of the pitch angle in the gait cycle (gait phase) according to the attribute.

For example, the male model 130M outputs the estimation result regarding the degree of pronation/supination of the foot according to the input of the feature amount extracted from the latter half of the stance phase and the latter half of the swing phase in the gait waveform of the pitch angle. In other words, the male model 130M outputs the estimation result according to the input of the feature amount extracted from the gait waveform of the pitch angle in the male feature amount extraction period including immediately before toe off and immediately before heel strike. For example, the female model 130F outputs an estimation result regarding the degree of pronation/supination of the foot according to the input of the feature amount extracted from the first half of the stance phase in the gait waveform of the pitch angle. In other words, the female model 130F outputs the estimation result according to the input of the feature amount extracted from the gait waveform of the pitch angle in the female feature amount extraction period including the period immediately after the heel strike and the period of single-leg support.

For example, the young person model 130Y outputs the estimation result regarding the degree of pronation/supination of the foot according to the input of the feature amount extracted from the latter half of the stance phase and the latter half of the swing phase in the gait waveform of the pitch angle. In other words, the young person model 130Y outputs the estimation result regarding the degree of pronation/supination of the foot according to the input of the feature amount extracted from the gait waveform of the pitch angle in the young feature amount extraction period including the period immediately before toe off and the period immediately before heel strike. For example, the elderly person model 130S outputs the estimation result regarding the degree of pronation/supination of the foot according to the input of the feature amount extracted from the first half of the stance phase and the latter half of the swing phase in the gait waveform of the pitch angle. In other words, the elderly person model 130S outputs the estimation result according to the input of the feature amount extracted from the gait waveform of the pitch angle in the elderly person feature amount extraction period including the period immediately after the heel strike and the period immediately before heel strike. In a case where age is used as the attribute, in the latter half of the swing phase (immediately before heel strike), there is a tendency that the gait phases in which the features appear in the young and the elderly overlap. Therefore, in a case where age is used as the attribute, features extracted from the latter half of the stance phase (the young) and the first half of the stance phase (the elderly) in which the gait phases in which the features appear are different between the young and the elderly may be used.

In the present example embodiment, an inference model that is trained with a data set of a feature amount extracted from the time series data of the pitch angle measured by the data acquisition device 11 and CPEI obtained from the foot pressure distribution measured by the pressure sensor is generated in advance. For example, an inference model that outputs the degree of pronation/supination of the foot according to the input of the feature amount extracted from the pitch angle time series data in a gait cycle (gait phase) in which the feature peculiar to each attribute appears is generated in advance. For example, an average value such as an arithmetic average, or a weighted average, an integral value, or the like of the pitch angle extracted from the time series data of the pitch angle in a gait cycle (gait phase) in which the feature peculiar to each attribute appears is used as the feature amount. For example, for a plurality of subjects, a large amount of data having a pitch angle as an explanatory variable and CPEI as an objective variable is measured, and an inference model trained with the data as teacher data is generated. For example, an inference model that classifies the state of the foot into any one of pronation, supination, and normal according to the estimation value of the CPEI, and outputs the result as the degree of pronation/ supination of the foot may be generated.

Figure 13:
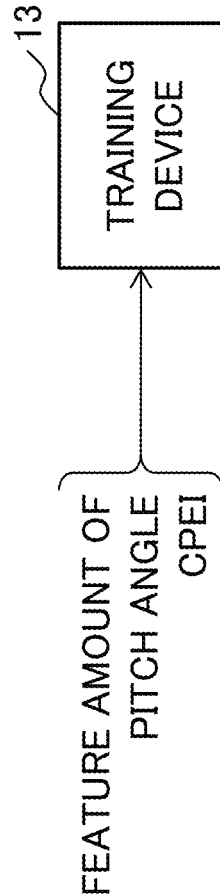
FIG. 13 is a conceptual diagram illustrating an example of training of an inference model used by the estimation device of the estimation system according to the first example embodiment.

FIG. 13 is a conceptual diagram illustrating an example in which a training device 13 is trained with a data set of the feature amount (explanatory variable) of the pitch angle and the CPEI (objective variable) as teacher data. In the present example embodiment, the training device 13 is trained with teacher data regarding a plurality of subjects, and the inference model 130 that outputs the estimation result regarding the degree of pronation/supination of the foot according to the input of the feature amount of the pitch angle is generated in advance.

The inference model 130 generated in advance is stored in the storage unit 123. For example, the inference model 130 may be stored in the estimation device 12 at the timing of shipment of a product from the factory, calibration before the user uses the estimation device 12, or the like. The estimation device 12 estimates the degree of pronation/supination of the foot by inputting, to the inference model 130, the feature amount extracted from the time series data of the pitch angle generated using the sensor data measured by the data acquisition device 11. For example, the estimation device 12 outputs an estimation result classified into any of three classifications of pronation, normal, and pronation as the degree of pronation/supination of the foot. For example, the estimation device 12 may output an estimation value of CPEI or a feature amount of a pitch angle as the degree of pronation/supination of the foot.

The feature amount extraction unit 125 extracts a feature amount used for estimation of the physical condition according to the attribute of the user from the gait waveform for one gait cycle. Specifically, the feature amount extraction unit 125 extracts a feature amount used for estimating the physical condition from the gait waveform for one gait cycle using the inference model for each attribute stored in the storage unit 123. For example, the feature amount extraction unit 125 extracts a feature amount used for estimating the degree of pronation/supination from the gait waveform of the pitch angle (angle waveform in the coronal plane) using the inference model according to the attribute of the user. For example, the feature amount extraction unit 125 extracts an integral value, an average value, or the like of the pitch angle from the gait waveform of the pitch angle (angle waveform in the coronal plane) as the feature amount used for estimating the degree of pronation/supination using the inference model according to the attribute of the user.

The inference unit 127 inputs the feature amount of the gait waveform (angle waveform in the coronal plane) of the pitch angle extracted by the feature amount extraction unit 125 to the inference model 130 for each attribute, and estimates the estimation result regarding the physical condition. For example, the inference unit 127 inputs the feature amount of the gait waveform (angle waveform in the coronal plane) of the pitch angle extracted by the feature amount extraction unit 125 to the inference model 130 for each attribute, and estimates the estimation result regarding the degree of pronation/supination of the foot. The inference unit 127 outputs an estimation result. The estimation result by the inference unit 127 is output to a host system, a server in which a database is constructed, a mobile terminal of a user who is an acquisition source of a gait waveform, or the like. The output destination of the estimation result by the inference unit 127 is not particularly limited.

Figure 14:
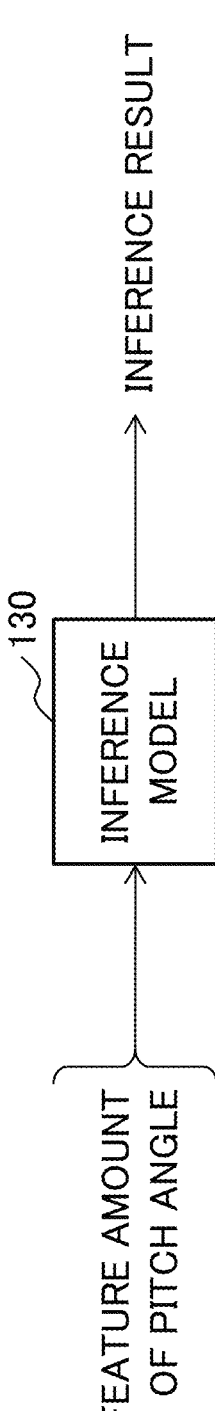
FIG. 14 is a conceptual diagram illustrating an example of estimation of the degree of pronation/supination of the foot by the estimation device of the estimation system according to the first example embodiment.

FIG. 14 is a conceptual diagram illustrating an example in which the estimation result regarding the degree of pronation/supination of the foot is output by inputting the feature amount of the pitch angle for each attribute to the inference model 130 generated in advance. For example, the estimation result regarding the degree of pronation/supination of the foot includes a determination result of the pronation/supination/normal of the foot. For example, the estimation result regarding the degree of pronation/supination of the foot includes recommendation information for advancing a hospital suitable for examination according to the determination result of the pronation/supination/normal of the foot. For example, the estimation result regarding the degree of pronation/supination of the foot may be a value of the pitch angle or CPEI. The above estimation result is an example, and does not limit the estimation result output from the inference model 130 by inputting the feature amount of the pitch angle for each attribute.

For example, in response to the input of the feature amount of the pitch angle for each attribute, the inference model 130 outputs recommendation information for advancing an appropriate hospital according to the determination result of the pronation/supination/normal of the foot as the estimation result regarding the degree of the pronation/supination of the foot. For example, the inference model 130 outputs the value of the pitch angle and the CPEI as the estimation result regarding the degree of pronation/supination of the foot according to the input of the feature amount of the pitch angle for each attribute. The estimation result of the inference model 130 described above is an example, and the estimation result output from the inference model 130 by inputting the feature amount of the pitch angle for each attribute is not limited.

(Operation)

Figure 15:
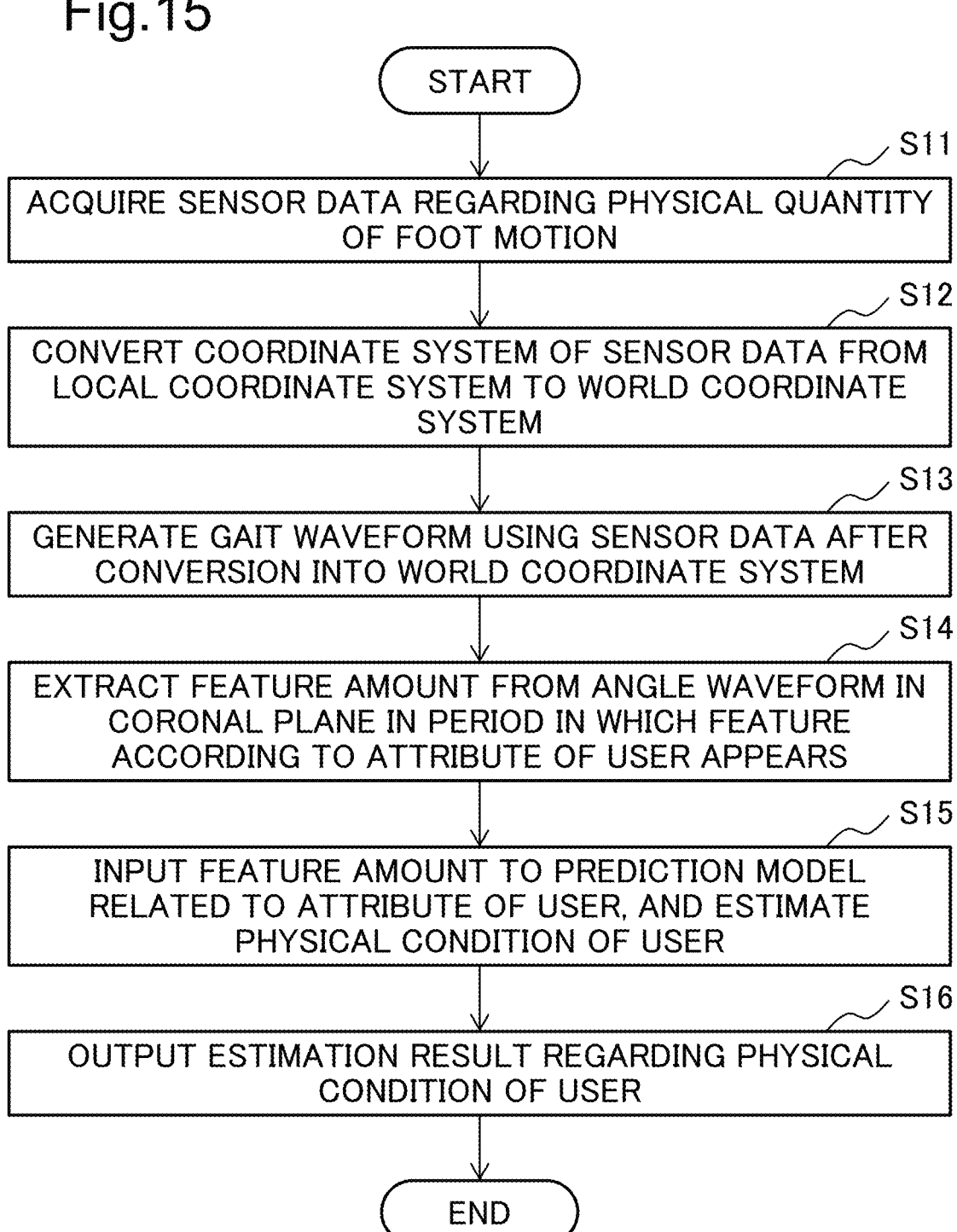
FIG. 15 is a flowchart for explaining an example of the operation of the estimation device of the estimation system according to the first example embodiment.

Next, an operation of the estimation device 12 of the estimation system 1 of the present example embodiment will be described with reference to the drawings. FIG. 15 is a flowchart for explaining an outline of the operation of the estimation device 12. Details of the operation of the estimation device 12 are as described regarding the above-described configuration.

In FIG. 15, first, the estimation device 12 acquires sensor data regarding a physical quantity regarding the motion of the foot from the data acquisition device 11 (step S11).

Next, the estimation device 12 converts the coordinate system of the acquired sensor data from the local coordinate system set in the data acquisition device 11 to the world coordinate system (step S12).

Next, the estimation device 12 generates a gait waveform using the time series data of the sensor data after conversion into the world coordinate system (step S13).

Next, the estimation device 12 extracts a feature amount from the angle waveform of the coronal plane (gait waveform of the pitch angle) in a period (gait phase) in which the feature according to the attribute of the user appears (step S14).

Next, the estimation device 12 inputs the extracted feature amount to the inference model 130 according to the attribute of the user, and estimates the physical condition of the user (step S15). For example, the estimation device 12 inputs a feature amount to the inference model 130 according to the attribute of the user, and estimates the degree of pronation/supination of the foot of the user.

Next, the estimation device 12 outputs an estimation result regarding the physical condition of the user (step S16). For example, the estimation device 12 outputs an estimation result regarding the degree of pronation/supination of the foot (step S16).

Verification Example

Next, a verification example of a relationship between CPEI (inference value) inferred based on the feature amount extracted based on the sensor data measured by the data acquisition device 11 and CPEI (true value) measured by the pressure-sensitive sensor will be described.

Figure 16:
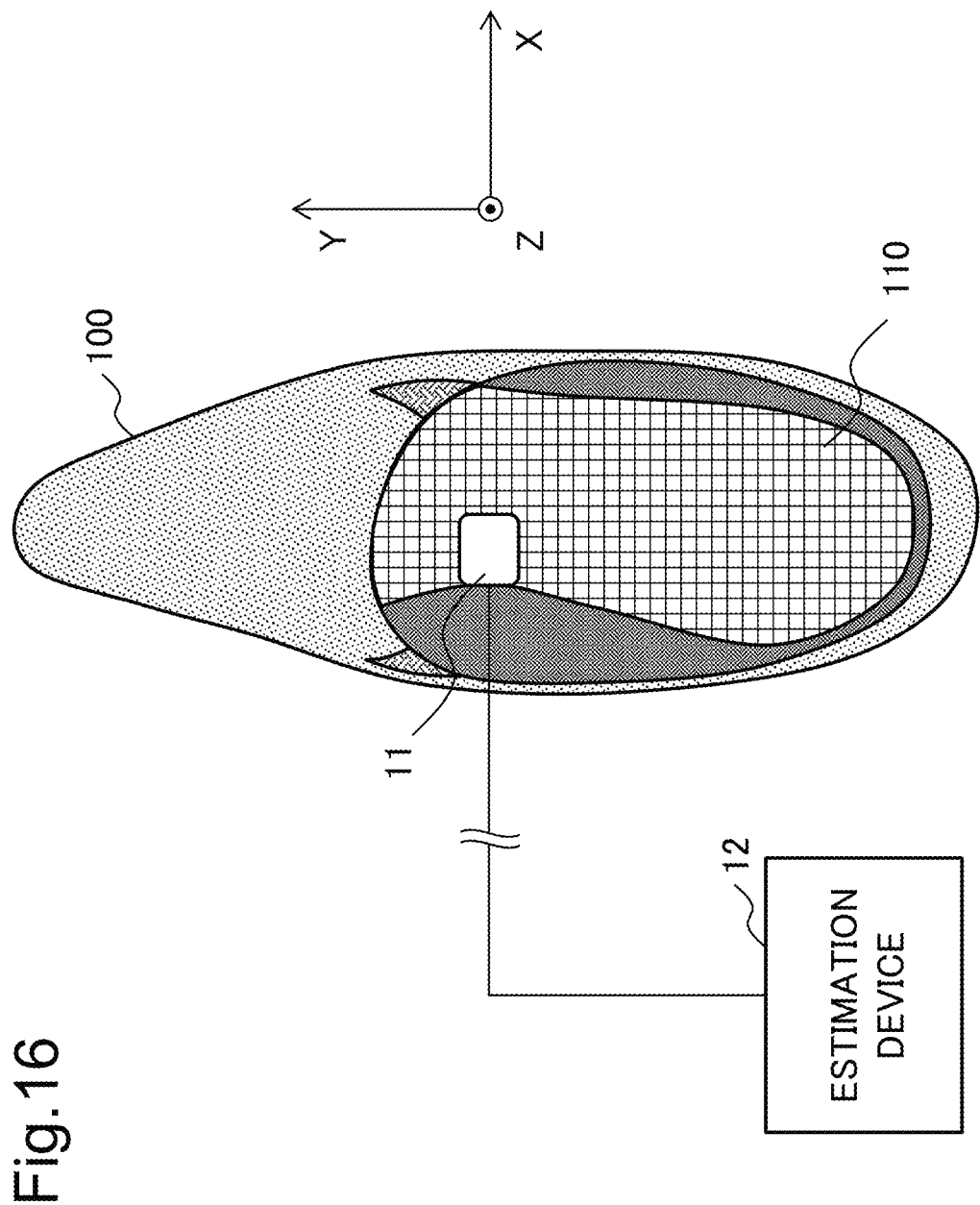
FIG. 16 is a conceptual diagram illustrating an example in which the data acquisition device and the pressure-sensitive sensor of the estimation system according to the first example embodiment are disposed in the footwear.

FIG. 16 is a conceptual diagram illustrating an arrangement example of a pressure-sensitive sensor 110 and the data acquisition device 11 used in the present verification example. In the present verification example, the pressure-sensitive sensor 110 capable of measuring the foot pressure distribution is inserted as a footbed of the shoe 100, and the data acquisition device 11 is mounted at a position on the back side of the arch of the foot.

In the present verification example, the relationship between the CPEI (inference value) inferred based on the feature amount extracted from the time series data of the pitch angle and the measured value (true value) of the CPEI for 36 subjects for each gender (72 subjects in total) was verified. In the present verification example, verification was performed for 12 subjects (72 subjects in total) for each of persons of 20 to 30 years old (the young), persons of 40 to 50 years old (middle-aged persons), and persons of 60 to early 70 years old (the elderly) for each gender.

The average age of the subjects in the present verification example was 44.3 years old, the youngest was 20 years old, and the oldest was 71 years old. The body weight of the subject in the present verification example was 62.9 kg (kilogram) on average, 115 kg at maximum, and 40 kg at minimum. The height of the subject in the present verification example was 165.0 cm (centimeter) on average, 192 cm at maximum, and 143 cm at minimum. The size of the foot of the subject in the present verification example was 25.3 cm on average, 22.5 cm at minimum, and 29.0 cm at maximum. The BMI (body mass index) of the subject in the present verification example was 22.9 on average, 36.3 at maximum, and 17.3 at minimum.

In the present verification example, each subject was caused to perform three trials of linearly walking to a turning point 15 m (meter) ahead of the start point, turning back at the turning point, and linearly walking to the start point. Each subject was caused to walk at different gait speeds in three trials. The gait speed in the three trials includes three patterns of normal gait, slow gait, and fast gait. In order to eliminate physical bias and psychological bias, the order of the gait speed was changed for each subject. The average value of all the number of steps in one trial was calculated in preparation for the possibility that the whole measurement value of one step may be missed. One point of data (one set of average waveform) was extracted from one trial.

The estimation device 12 generates nine types of gait waveforms of accelerations in three axial directions, angular velocities around the three axes, and angles around the three axes (plantar angle). In the present verification example, the correlation with the CPEI was evaluated for each gait cycle (gait phase) from nine types of gait waveforms. In evaluating the correlation, an average value of correlation coefficients was finally calculated using the Leave-one-subject-out method in order to eliminate bias due to data distribution. A threshold value is set in advance for the correlation coefficient, and a gait phase that may have a correlation in which the correlation coefficient exceeds the threshold value is selected. For a section (also referred to as a gait phase cluster) continuously exceeding the threshold value over a plurality of gait phases, the feature amount for each gait phase cluster was calculated. Regarding the gait phase cluster, an integral average value of measurement values in a plurality of gait phases constituting the gait phase cluster was set as the feature amount.

Figure 17:
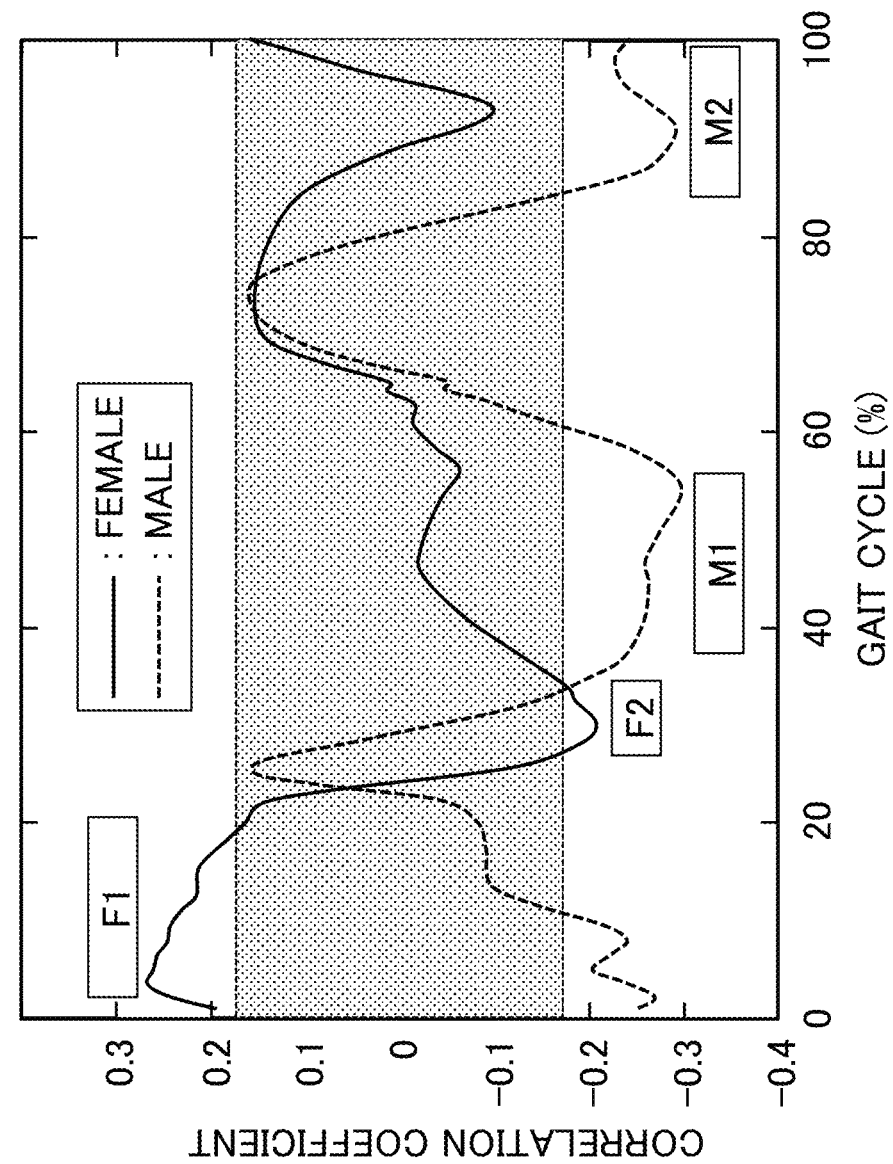
FIG. 17 is a graph illustrating a correlation coefficient between CPEI (inference value) inferred based on sensor data measured by the data acquisition device and CPEI (true value) measured by the pressure-sensitive sensor of the estimation system according to the first example embodiment.

FIG. 17 is a graph illustrating a correlation coefficient for each gender between CPEI (inference value) inferred based on the feature amount extracted from the time series data of the pitch angle and CPEI (true value) measured by the pressure-sensitive sensor 110. In FIG. 17, the correlation coefficient between CPEI (inference value) and CPEI (true value) is plotted separately for the female (solid line) and the male (dotted line). In FIG. 17, the boundary lines at the upper limit and the lower limit of the hatched range correspond to the threshold values. In a section beyond the hatched range (a section of the gait phase in which the correlation coefficient exceeds the threshold value), the correlation between the CPEI (inference value) and the CPEI (true value) is high. That is, the feature amount of the CPEI for each attribute (gender) can be extracted from the section of the gait phase in which the correlation coefficient exceeds the threshold value.

For the female (solid line), the correlation coefficient exceeds the threshold value in the first half of the stance phase (a period F1 immediately after heel strike and a period F2 of single-leg support). On the other hand, regarding the male (dotted line), the correlation coefficient exceeds the threshold value in the latter half of the stance phase (a period M1 immediately before toe off) and the latter half of the swing phase (a period M2 immediately before heel strike). As described above, the section of the gait phase correlated with the CPEI is different between the female (solid line) and the male (dotted line). In the present verification example, regarding the female (solid line), the inference model is generated using the feature amount extracted from the first half of the stance phase (the period F1 immediately after the heel strike and the period F2 of single-leg support). On the other hand, for the male (dotted line), an inference model was generated using feature amounts extracted from the latter half of the stance phase (the period M1 immediately before toe off) and the latter half of the swing phase (the period M2 immediately before heel strike).

Figure 18:
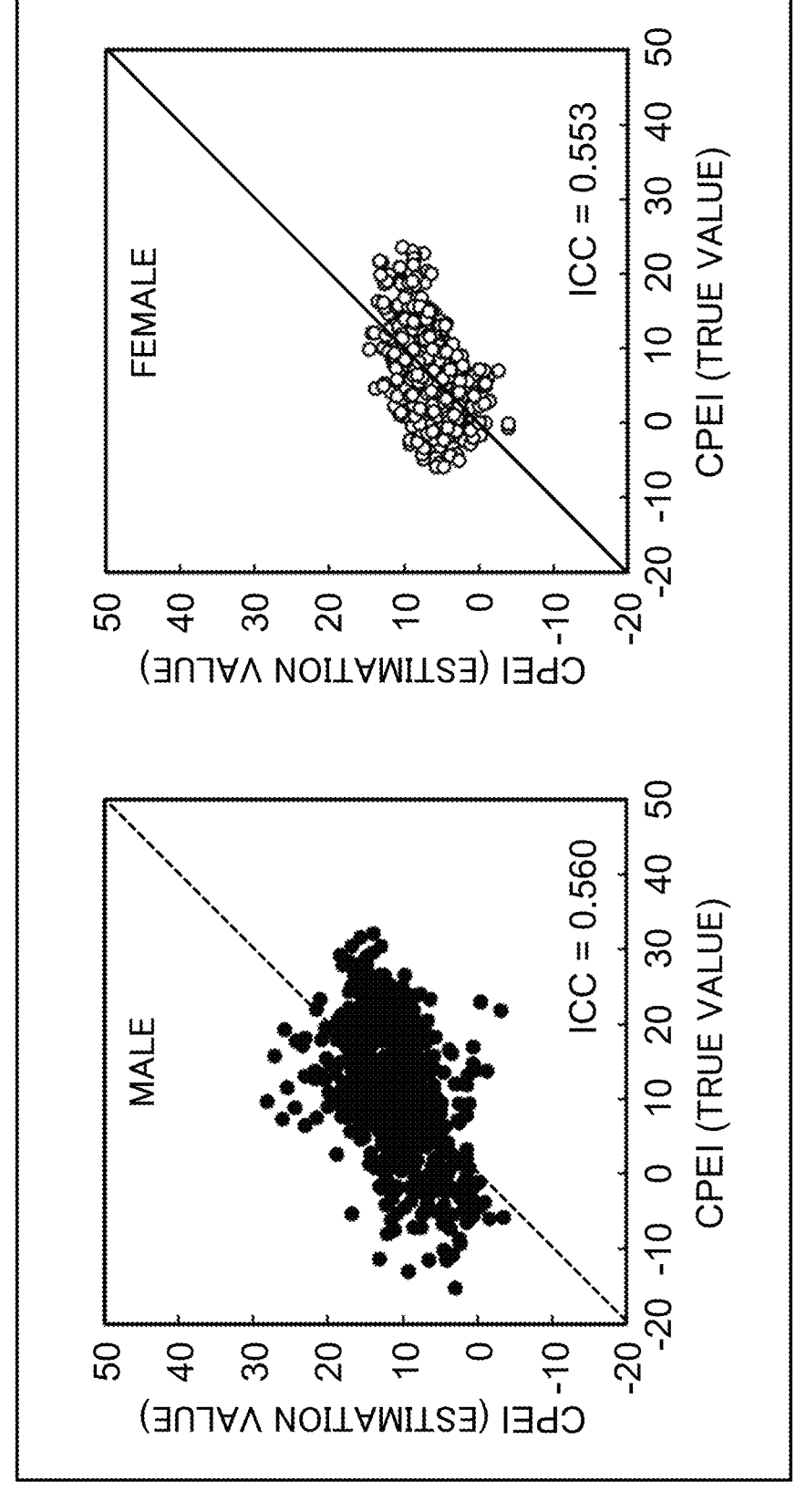
FIG. 18 is a graph illustrating a correlation between CPEI (estimation value) estimated by the estimation device of the estimation system of the first example embodiment and CPEI (true value) based on a measurement result of the pressure-sensitive sensor.
Figure 19:
FIG. 19 is a graph illustrating a result of verifying a correlation between CPEI (estimation value) estimated by the estimation device of the estimation system of the first example embodiment and CPEI (true value) based on a measurement result by a pressure-sensitive sensor 110 with a Z score.

FIG. 18 is a graph illustrating a correlation between CPEI (estimation value) estimated by inputting the feature amount extracted from the section of the gait phase in which the feature for each gender appears to the inference model for each gender and CPEI (true value) based on the measurement result of the pressure-sensitive sensor 110. FIG. 18 illustrates a result of verifying the correlation between the CPEI (estimation value) and the CPEI (true value) using leave one subject out cross validation. For the male, the intraclass correlation coefficient (ICC) was 0.560. For the female, the ICC was 0.553. FIG. 19 is a graph illustrating a result of verifying the correlation between the CPEI (estimation value) and the CPEI (true value) by the Z score. For the male, the ICC was 0.627. On the other hand, for the female, the ICC was 0.628. The results of FIGS. 18 and 19 indicate that there is a moderate coincidence between the CPEI (estimation value) estimated using the feature amount extracted from the section of the gait phase in which the feature for each gender appears and the CPEI (true value) measured using the pressure-sensitive sensor 110. That is, the degree of pronation/supination (CPEI) can be estimated using the feature amount extracted from the section of the gait phase in which the feature for each gender appears.

Figure 20:
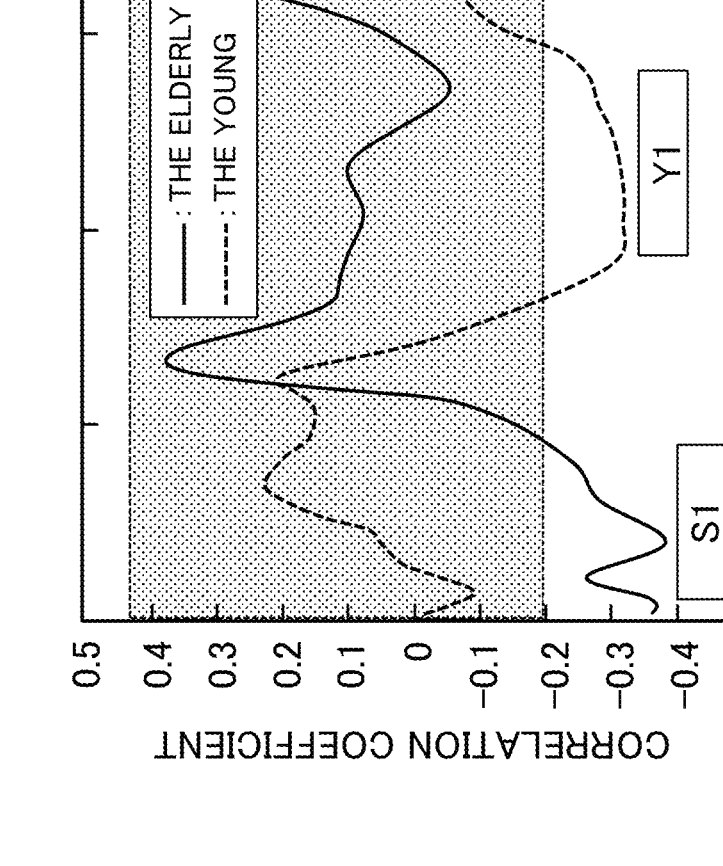
FIG. 20 is a graph illustrating a correlation coefficient between CPEI (inference value) inferred based on sensor data measured by the data acquisition device and CPEI (true value) measured by the pressure-sensitive sensor of the estimation system according to the first example embodiment.

FIG. 20 is a graph illustrating a correlation coefficient for each age between CPEI (inference value) inferred based on the feature amount extracted from the time series data of the pitch angle and CPEI (true value) measured by the pressure-sensitive sensor 110. In FIG. 20, the correlation coefficient between CPEI (inference value) and CPEI (true value) is separately plotted for the elderly (solid line) and the young (dotted line). In FIG. 20, the boundary lines at the upper limit and the lower limit of the hatched range are set as the threshold values. In a section beyond the hatched range (a section of the gait phase in which the correlation coefficient exceeds the threshold value), the correlation between the CPEI (inference value) and the CPEI (true value) is high. That is, the feature amount of the CPEI can be extracted from the section of the gait phase in which the correlation coefficient exceeds the threshold value.

For the elderly (solid line), the correlation coefficient exceeds the threshold value in the first half of the stance phase (a period S1 immediately after heel strike) and the latter half of the swing phase (a period S2 immediately before heel strike). On the other hand, for the young (dotted line), the correlation coefficient exceeds the threshold value in the latter half of the stance phase (a period Y1 immediately before toe off) and the latter half of the swing phase (a period Y2 immediately before heel strike). As described above, the section of the gait phase correlated with the CPEI is different between the elderly (solid line) and the young (dotted line). That is, for the elderly (solid line), an inference model may be generated using feature amounts extracted from the first half of the stance phase (the period S1 immediately after heel strike) and the latter half of the swing phase (the period S2 immediately before heel strike). On the other hand, for the young (dotted line), an inference model may be generated using feature amounts extracted from the latter half of the stance phase (the period Y1 immediately before the toe off ground) and the latter half of the swing phase (the period Y2 immediately before heel strike). In a case where age is used as the attribute, in the latter half of the swing phase (the period Y2 and the period S2 immediately before heel strike), there is a tendency that the gait phases in which the features appear in the young and the elderly overlap. Therefore, in a case where age is used as the attribute, the inference model may be generated using the feature amount extracted from the latter half of the stance phase (the period Y1 immediately before the toe off) for the elderly, and the latter half of the stance phase (the period Y1 immediately before the toe off) for the young. Although the result of the leave one subject out cross validation is omitted, the degree of pronation/supination can also be estimated using the feature amount extracted from the section of the gait phase in which the feature for each age appears.

Application Example

Next, an application example of the estimation system 1 of the present example embodiment will be described with reference to the drawings. The present application example is an example in which an estimation result regarding the degree of pronation/supination of the foot output by the estimation device 12 is displayed on a display device or utilized as big data. In the following example, it is assumed that the data acquisition device 11 is installed in a shoe of a pedestrian, and sensor data based on a physical quantity regarding a motion of a foot measured by the data acquisition device 11 is transmitted to a mobile terminal possessed by the pedestrian. The sensor data transmitted to the mobile terminal is data processed by application software or the like installed in the mobile terminal.

Figure 21:
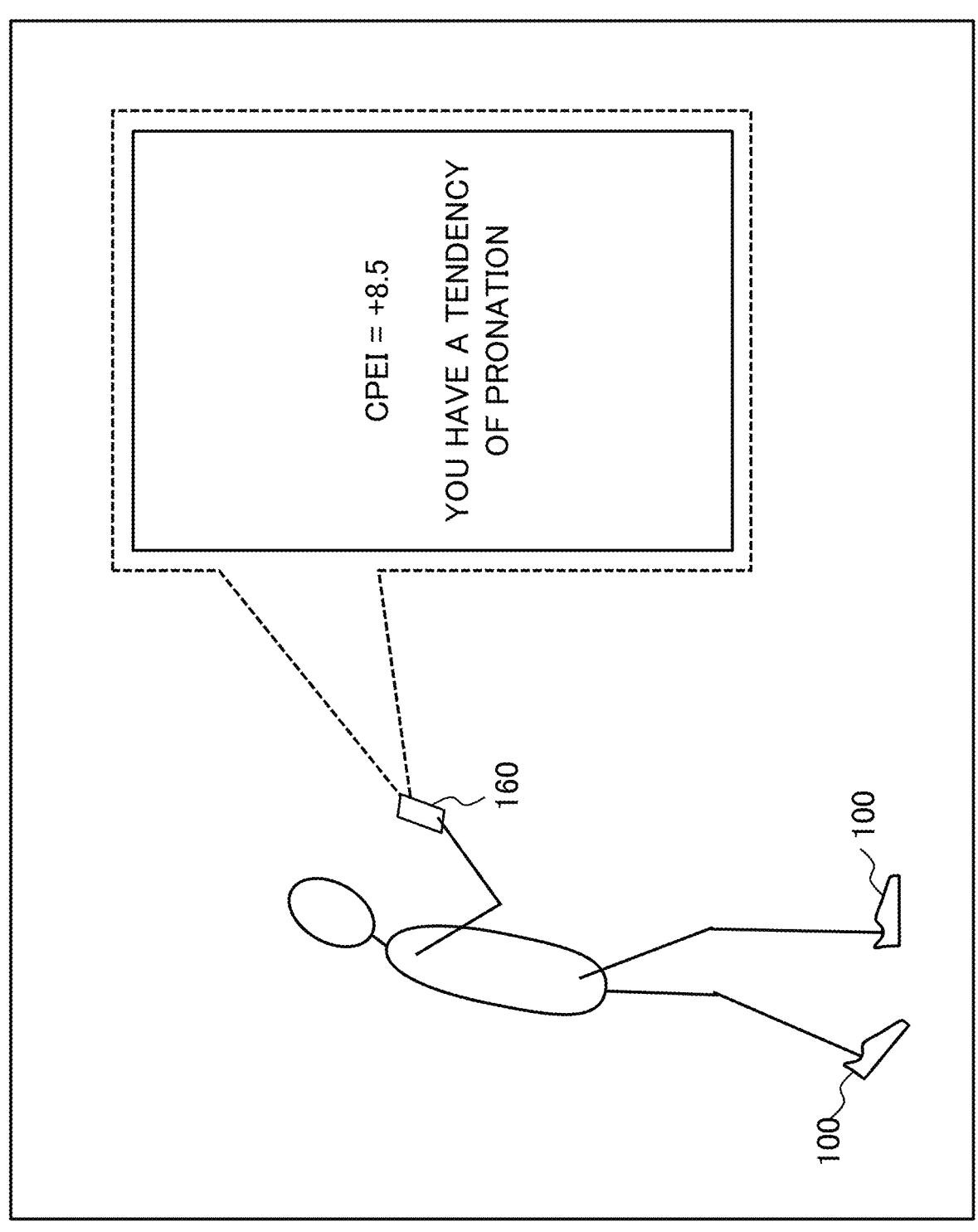
FIG. 21 is a conceptual diagram illustrating an example in which information based on the estimation result regarding the degree of pronation/supination of the foot inferred by the estimation device of the estimation system according to the first example embodiment is displayed on the display unit of the mobile terminal.

FIG. 21 illustrates an example in which the estimation result regarding the degree of pronation/supination of the foot of the pedestrian is displayed on the screen of a mobile terminal 160 of the pedestrian wearing the shoe 100 at which the data acquisition device (not illustrated) is installed. In the example of FIG. 21, a numerical value of "CPEI=+8.5" and a notification of "you have a tendency of pronation" are displayed on the screen of the mobile terminal 160 as the estimation result regarding the degree of pronation/supination of the foot. The pedestrian who has browsed the estimation result regarding the degree of pronation/supination of the foot displayed on the screen of the mobile terminal 160 can take an action according to the estimation result. For example, the pedestrian who has browsed the estimation result regarding the degree of pronation/supination of the foot displayed on the screen of the mobile terminal 160 can contact a medical institution or the like regarding his/her situation according to the estimation result. For example, the pedestrian who has browsed the estimation result regarding the degree of pronation/supination of the foot displayed on the screen of the mobile terminal 160 can exercise or walk in a manner suitable for the pedestrian according to the estimation result.

Figure 22:
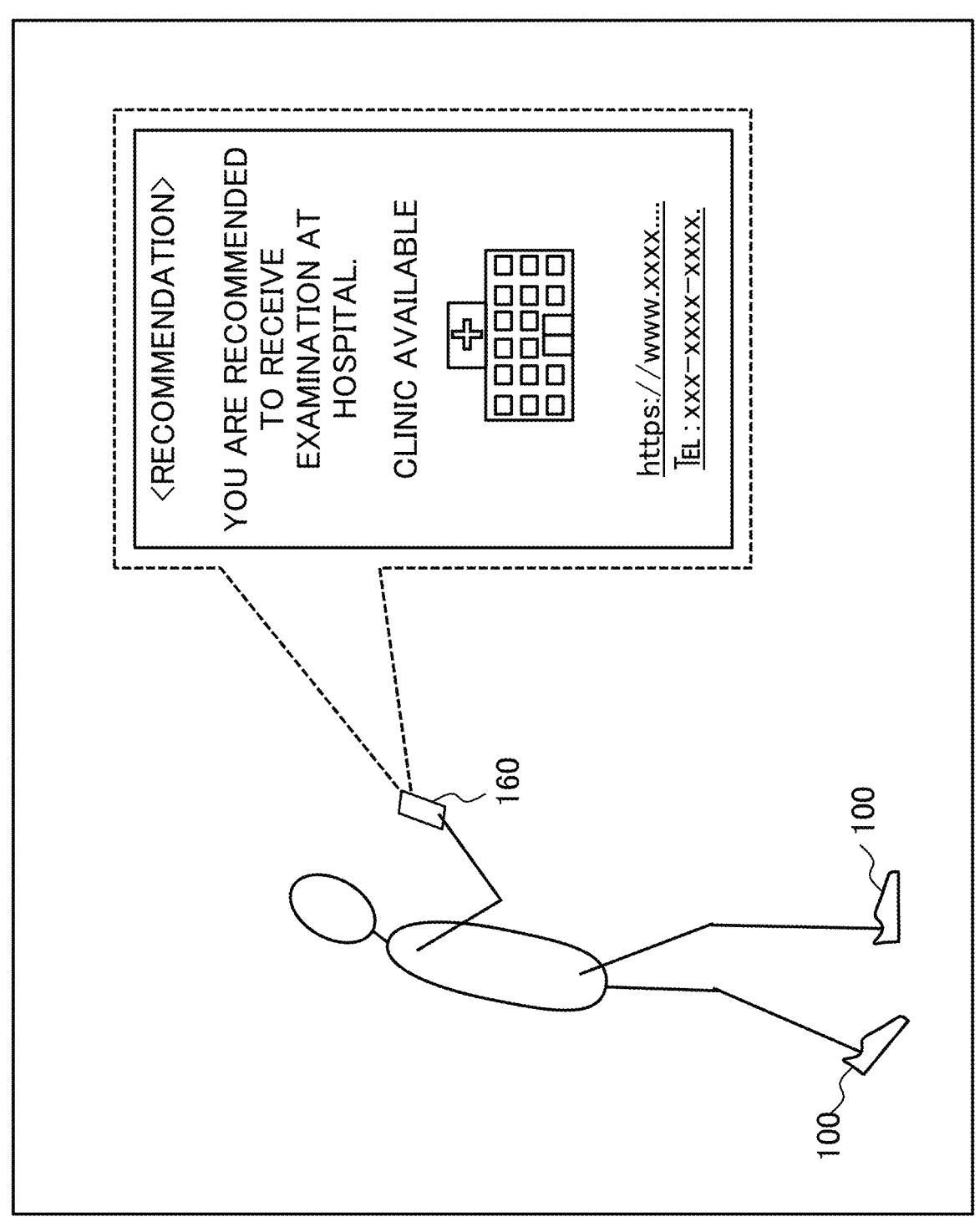
FIG. 22 is a conceptual diagram illustrating another example in which information based on the estimation result regarding the degree of pronation/supination of the foot inferred by the estimation device of the estimation system according to the first example embodiment is displayed on the display unit of the mobile terminal.

FIG. 22 illustrates an example in which information according to the estimation result regarding the degree of pronation/supination of the foot of the pedestrian is displayed on the screen of the mobile terminal 160 of the pedestrian wearing the shoe 100 at which the data acquisition device (not illustrated) is installed. For example, information recommending that a pedestrian receives a medical examination at a hospital is displayed on the screen of the mobile terminal 160 according to the progress status of the pronation/supination of the foot. For example, depending on the progress status of the pronation/supination of the foot, a link destination or a telephone number to a site of a hospital that the pedestrian can receive a medical examination may be displayed on the screen of the mobile terminal 160. For example, the pedestrian who has browsed information related to the estimation result regarding the degree of pronation/supination of the foot displayed on the screen of the mobile terminal 160 can act according to the information.

Figure 23:
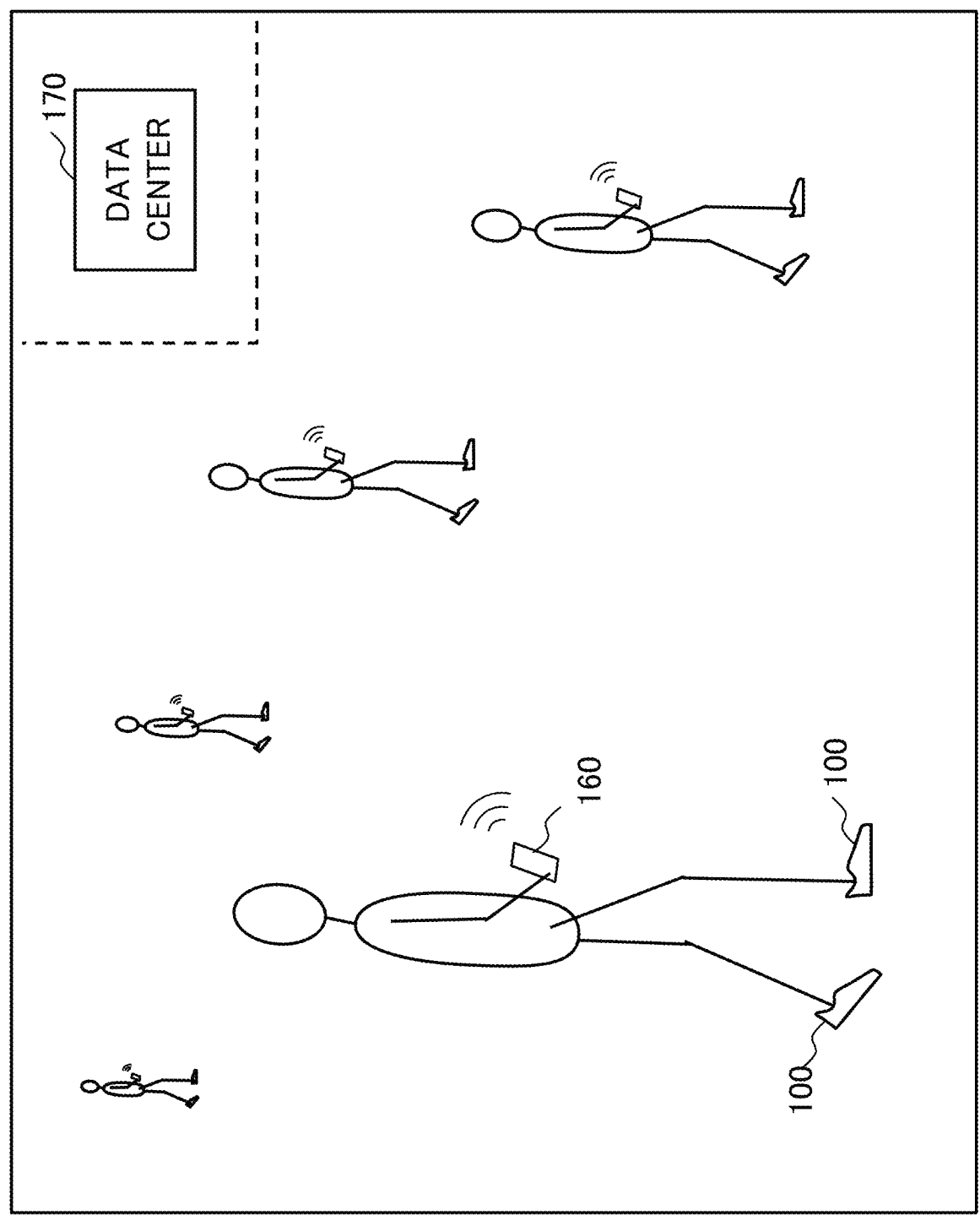
FIG. 23 is a conceptual diagram illustrating an example in which data based on an estimation result regarding a degree of pronation/supination of a foot inferred by the estimation device of the estimation system according to the first example embodiment is transmitted to a data center.

FIG. 23 illustrates an example in which information based on sensor data measured by a data acquisition device (not illustrated) is transmitted from the mobile terminal 160 of each of a plurality of pedestrians each wearing the shoe 100 at which the data acquisition device is installed to a data center 170. For example, the mobile terminal 160 transmits sensor data measured by the data acquisition device, an estimation value of CPEI, and an estimation result regarding the degree of pronation/supination of the foot of the pedestrian to the data center 170. For example, data transmitted to the data center 170 is accumulated in a database. For example, data accumulated in the database is utilized as big data.

In the present example embodiment, an example of estimating the degree of pronation/supination as the physical condition is described. The method of the present example embodiment can also be applied to estimation of a physical condition other than the degree of pronation/supination. For example, the degree of hallux valgus tends to be mainly caused by the influence of footwear for the female, and to be mainly caused by the influence of injury for the male. Therefore, it is estimated that the degree of hallux valgus varies in the section in which the feature appears depending on the gender. For example, the case where the standing work is mainly performed and the case where the sitting work is mainly performed have different tendencies of O legs and X legs. In a case where such an assumption is made, it is estimated that the degree of the O leg or the X leg differs in a section in which the feature appears depending on a social attribute such as a job category.

As described above, the estimation system of the present example embodiment includes the data acquisition device and the inference device. The data acquisition device is installed at a foot portion of the user, and measures a spatial acceleration and a spatial angular velocity. The data acquisition device generates sensor data based on the measured spatial acceleration and the measured spatial angular velocity to transmit the generated sensor data to the estimation device. The estimation device includes the detection unit, the feature amount extraction unit, the storage unit, and the inference unit. The detection unit detects a gait event from time series data of sensor data based on the motion of the foot of the user. The detection unit extracts a gait waveform for one gait waveform based on the detected gait event. The feature amount extraction unit extracts a feature amount according to the attribute of the user in a section in which the feature of the physical condition according to the attribute of the user appears from the gait waveform extracted by the detection unit. The storage unit stores an inference model that outputs the physical condition of the user according to the input of the feature amount extracted according to the attribute of the user. The inference unit inputs the feature amount extracted according to the attribute of the user to the inference model stored in the storage unit to estimate the physical condition of the user.

The estimation system of the present example embodiment estimates the physical condition of the user according to the attribute by using sensor data based on the motion of the foot measured by a data acquisition device installed at a foot portion of the user. That is, the estimation system of the present example embodiment can estimate the physical condition according to the attribute based on the sensor data measured along with gait.

In an aspect of the present example embodiment, the inference unit inputs the feature amount extracted from the gait waveform of the user to the inference model that outputs the estimation result regarding the physical condition according to the attribute according to the input of the feature amount extracted according to the attribute. The estimation unit estimates the physical condition of the user based on the estimation result output from the inference model. According to the present aspect, it is possible to estimate the physical condition reflecting the attribute of the user by inputting the feature amount extracted from the gait waveform according to the attribute of the user to the inference model generated for each attribute.

In an aspect of the present example embodiment, the feature amount extraction unit extracts a feature amount from a gait waveform regarding an angle in the coronal plane. The inference unit estimates the degree of pronation/supination of the foot using the feature amount extracted from the gait waveform regarding the angle in the coronal plane. According to the present aspect, the degree of pronation/supination of the foot reflecting the attribute of the user can be estimated as the physical condition.

In an aspect of the present example embodiment, the inference unit inputs a feature amount extracted from the gait waveform of the user to an inference model trained with a data set regarding a plurality of subjects, and estimates the degree of pronation/supination of the foot of the user. The data set has the feature amount extracted from the gait waveform regarding the angle in the coronal plane in the section in which the physical condition feature according to the attribute appears as the explanatory variable, and the center of pressure excursion index obtained from the foot pressure distribution measured by the pressure sensor as the objective variable. According to the present aspect, the degree of pronation/supination of the foot reflecting the attribute of the user can be estimated using the inference model trained with the data set regarding the plurality of subjects.

In an aspect of the present example embodiment, the estimation unit estimates the degree of pronation/supination of the user using the inference model for each gender. In a case where the user is a female, the feature amount extraction unit extracts a feature amount in a female feature amount extraction period including a period immediately after heel strike and a period of single-leg support from a gait waveform regarding an angle in the coronal plane. Then, the inference unit inputs the feature amount extracted by the feature amount extraction unit to a female inference model trained with the feature amount extracted in the female feature amount extraction period for a plurality of female subjects to estimate the degree of pronation/supination of the user. In a case where the user is a male, the feature amount extraction unit extracts a feature amount in a male feature amount extraction period including a period immediately before toe off and a period immediately before heel strike. Then, the inference unit inputs the feature amount extracted by the feature amount extraction unit to a male inference model trained with the feature amount extracted from the male feature amount extraction period for a plurality of male subjects to estimate the degree of pronation/supination of the user.

In the present aspect, the feature is extracted from the gait waveform regarding the angle in the coronal plane in the period in which the unique feature according to the gender appears. Then, in the present aspect, the physical condition of the user is estimated using the inference model for each gender. Therefore, according to the present aspect, it is possible to estimate the degree of pronation/supination of the foot more reflecting the attribute (gender) of the user.

In an aspect of the present example embodiment, the estimation unit estimates the degree of pronation/supination of the user using the inference model for each age. In a case where the user is an elderly person, the feature amount extraction unit extracts a feature amount in an elderly person feature amount extraction period including a period immediately after heel strike and a period immediately before heel strike from a gait waveform regarding an angle in the coronal plane. Then, the inference unit inputs the feature amount extracted by the feature amount extraction unit to an elderly person inference model trained with the feature amount extracted in the elderly person feature amount extraction period for a plurality of elderly subjects, and estimates the degree of pronation/supination of the user. In a case where the user is a young person, the feature amount extraction unit extracts a feature amount in a young person feature amount extraction period including a period immediately before the toe off and a period immediately before heel strike from the gait waveform regarding the angle in the coronal plane. Then, the inference unit inputs the feature amount extracted by the feature amount extraction unit to a young person inference model trained with the feature amount extracted in the young person feature amount extraction period for a plurality of young subjects to estimate the degree of pronation/supination of the user.

In the present aspect, the feature is extracted from the gait waveform regarding the angle in the coronal plane in the period in which the unique feature according to the age appears. Then, in the present aspect, the physical condition of the user is estimated using the inference model for each age. Therefore, according to the present aspect, it is possible to estimate the degree of pronation/supination of the foot more reflecting the attribute (age) of the user.

In an aspect of the present example embodiment, the inference unit outputs a determination result indicating which of pronated/supinated or normal a foot is according to the value of the estimated center of pressure excursion index. According to the present aspect, it is possible to determine which of pronated/supinated or normal a foot is according to the estimation value of the center of pressure excursion index.

For example, the detection system of the present example embodiment can be applied to an order-made shoe. For example, the detection system of the present example embodiment can be applied to the use of causing the user to walk while wearing the guest shoe at which the data acquisition device is installed, and verifying the degree of pronation/supination of the foot of the user. When the data regarding the verification result of the degree of pronation/supination of the foot of the user is provided to the manufacturer who designs the shoe, the shoe can be designed according to the degree of pronation/supination of the foot of the user.

For example, the detection system of the present example embodiment can also be applied to the use of monitoring daily life of a user. For example, when a gait habit can be extracted or a change in shoes can be recommended according to the progress status of the pronation/supination of the foot in gait of the user, there is a possibility that the progress of the pronation/supination of the foot of the user can be suppressed. For example, in a case where the user uses the orthodontic appliance for pronation/supination of the foot, provision of information related to the degree of pronation/supination of the foot to the user may lead to reduction of the progress of symptoms and prevention of injuries.

For example, according to the detection system of the present example embodiment, by collecting estimation results of a large number of users and constructing a database of estimation results regarding the degree of pronation/supination of the foot, there is a possibility that information about the degree of pronation/supination of the foot can be utilized as big data. For example, when the degrees of pronation/supination and CPEI of the feet of a large number of users are stored in a database in association with shoes, data that can be utilized for shoe design, maintenance, and the like can be accumulated.

Second Example Embodiment

Figure 25:
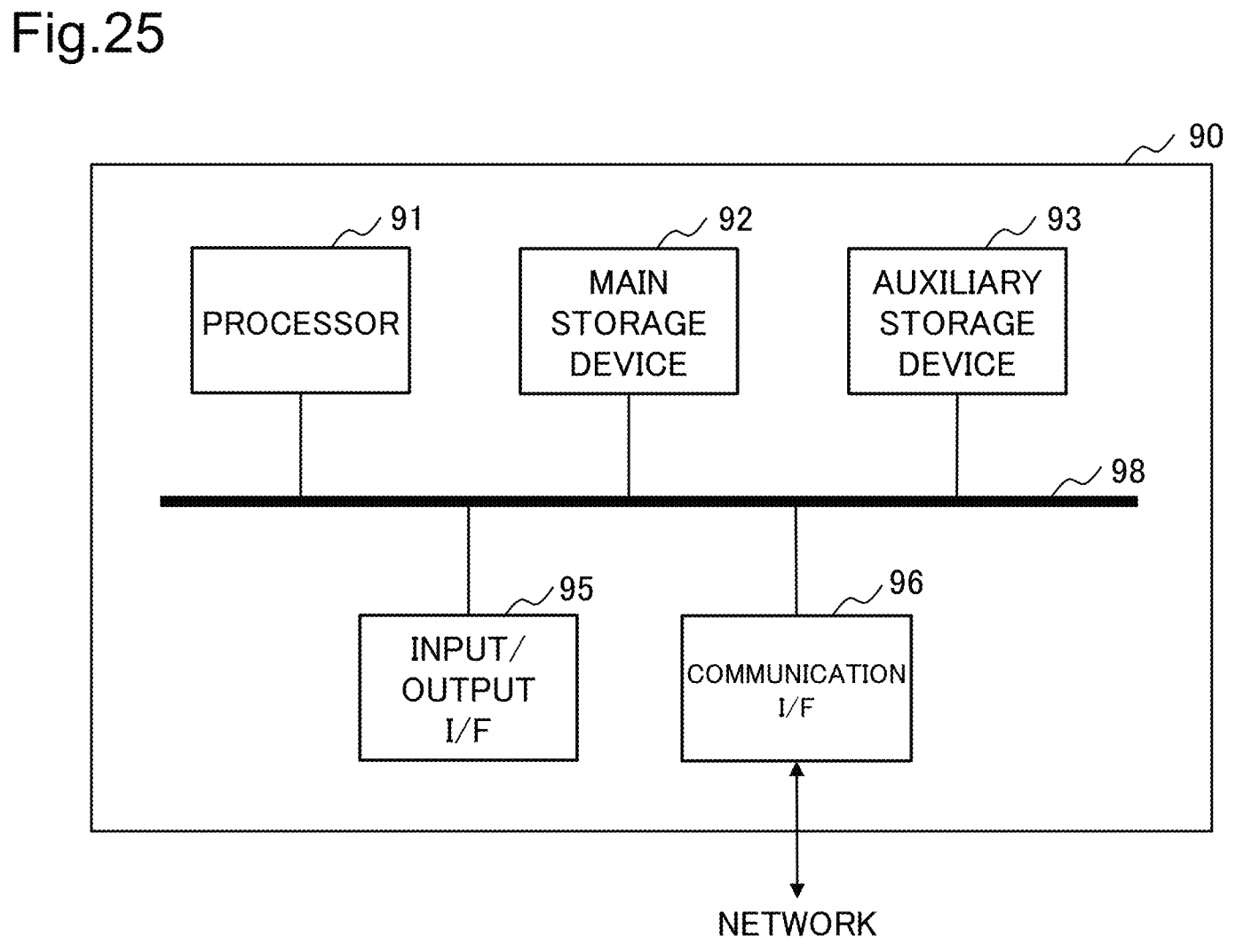

Next, an estimation device according to a second example embodiment will be described with reference to the drawings. The estimation device of the present example embodiment has a simplified configuration of the estimation device of the first example embodiment. FIG. 25 is a block diagram illustrating an example of a configuration of an estimation device 22 according to the present example embodiment. The estimation device 22 includes a feature amount extraction unit 225 and an inference unit 227.

The feature amount extraction unit 225 extracts a feature amount according to the attribute of the user in a section in which the feature of the physical condition according to the attribute of the user appears, from the gait waveform extracted from the time series data of the sensor data based on the motion of the foot of the user. The inference unit 227 estimates the physical condition of the user using the feature amount extracted according to the attribute of the user.

The estimation device of the present example embodiment, in the estimation system of the present example embodiment, estimates the physical condition of the user according to the attribute using the sensor data based on the motion of the foot measured by the data acquisition device installed at a foot portion of the user. That is, the estimation device of the present example embodiment can estimate the physical condition according to the attribute based on the sensor data measured with gait.
(Hardware)

A hardware configuration for executing the processing of the estimation device according to each example embodiment of the present invention will be described using an information processing device 90 of FIG. 25 as an example. The information processing device 90 in FIG. 25 is a configuration example for executing processing of the estimation device of each example embodiment, and does not limit the scope of the present invention.

As illustrated in FIG. 25, the information processing device 90 includes a processor 91, a main storage device 92, an auxiliary storage device 93, an input/output interface 95, and a communication interface 96. In FIG. 25, the interface is abbreviated as an interface (I/F). The processor 91, the main storage device 92, the auxiliary storage device 93, the input/output interface 95, and the communication interface 96 are data-communicably connected to each other via a bus 98. The processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92 and executes the developed program. In the present example embodiment, a software program installed in the information processing device 90 may be used. The processor 91 executes processing by the estimation device according to the present example embodiment.

The main storage device 92 has an area in which a program is developed. The main storage device 92 may be a volatile memory such as a dynamic random access memory (DRAM). A nonvolatile memory such as a magnetoresistive random access memory (MRAM) may be configured and added as the main storage device 92.

The auxiliary storage device 93 stores various pieces of data. The auxiliary storage device 93 includes a local disk such as a hard disk or a flash memory. Various pieces of data may be stored in the main storage device 92, and the auxiliary storage device 93 may be omitted.

The input/output interface 95 is an interface that connects the information processing device 90 with a peripheral device. The communication interface 96 is an interface that connects to an external system or a device through a network such as the Internet or an intranet in accordance with a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input information and settings. When the touch panel is used as the input device, the display screen of the display device may also serve as the interface of the input device. Data communication between the processor 91 and the input device may be mediated by the input/output interface 95.

The information processing device 90 may be provided with a display device that displays information. In a case where a display device is provided, the information processing device 90 preferably includes a display control device (not illustrated) that controls display of the display device.

The display device may be connected to the information processing device 90 via the input/output interface 95.

The above is an example of a hardware configuration for enabling the estimation device according to each example embodiment of the present invention. The hardware configuration of FIG. 25 is an example of a hardware configuration for executing arithmetic processing of the estimation device according to each example embodiment, and does not limit the scope of the present invention. A program for causing a computer to execute processing related to the estimation device according to each example embodiment is also included in the scope of the present invention. A recording medium in which the program according to each example embodiment is recorded is also included in the scope of the present invention. The recording medium can be achieved by, for example, an optical recording medium such as a compact disc (CD) or a digital versatile disc (DVD). The recording medium may be achieved by a semiconductor recording medium such as a Universal Serial Bus (USB) memory or a secure digital (SD) card, a magnetic recording medium such as a flexible disk, or another recording medium. In a case where the program executed by the processor is recorded in the recording medium, the recording medium is a program recording medium.

The components of the estimation device of each example embodiment can be combined in any manner. The components of the estimation device of each example embodiment may be achieved by software or may be achieved by a circuit.

While the present invention is described with reference to example embodiments thereof, the present invention is not limited to these example embodiments. It will be understood by those of ordinary skill in the art that various changes in form and details may be made therein without departing from the spirit and scope of the present invention as defined by the claims.

REFERENCE SIGNS LIST

1 estimation system
11 data acquisition device
12, 22 estimation device
111 acceleration sensor
112 angular velocity sensor
113 control unit
115 data transmission unit
121 detection unit
123 storage unit
125, 225 feature amount extraction unit
127, 227 inference unit

What is claimed is:

1. An estimation device comprising:
a communication interface;
a memory storing instructions; and
a processor connected to the at least one memory and configured to execute the instructions to:
receive, via a communication interface, time-series sensor data including three-axis acceleration and angular velocity from a data acquisition device installed in footwear at a back-of-arch position of a foot of a user;
convert the received sensor data from a local coordinate system of the data acquisition device to a world coordinate system;
detect gait events in the converted, received sensor data, the detected gait events including heel-strike events and toe-off events;

generate, for one gait cycle normalized between consecutive ones of the heel-strike events, a gait waveform of a pitch angle representing rotation about a Y-axis in a coronal plane;
extract, from the pitch-angle gait waveform, a feature amount according to an attribute of the user selected from gender and age in a section defined as a predetermined sub-range of the normalized gait cycle identified relative to the detected heel-strike and toe-off events, the feature amount comprising at least one of an arithmetic mean or an integral of the pitch angle;
input the feature amount to an attribute-specific inference model stored in the memory, the model being trained with a data set in which a training feature amount is an explanatory variable and a center of pressure excursion index (CPEI) obtained from a foot pressure distribution measured by a pressure sensor is an objective variable for a plurality of subjects;
execute the attribute-specific inference model to estimate the CPEI for the user based on the inputted feature amount;
classify a degree of pronation/supination of a foot of the user based on the estimated CPEI, the classification being determined using thresholds stored in the memory including a pronation threshold and a supination threshold; and
cause an output unit to present the estimated CPEI and the classification among pronation/normal/supination.

2. The estimation device according to claim 1, wherein the processor is configured to execute the instructions to:
input the feature amount extracted from the gait waveform of the user to an inference model that outputs an estimation result regarding a physical condition according to the attribute according to an input of the feature amount extracted according to the attribute; and
estimate the physical condition of the user based on the estimation result output from the inference model.

3. The estimation device according to claim 1, wherein the processor is configured to execute the instructions to:
estimate a physical condition of the user by using the inference model learned by machine learning; and
output information to assist the user's decision of contacting a medical institution.

4. An estimation system comprising:
the estimation device according to claim 1; and
a data acquisition device that is configured to be installed at a foot portion of the user, is configured to measure the acceleration and the angular velocity, is configured to generate the time-series sensor data based on the measured acceleration and the measured angular velocity, and is configured to transmit the generated time-series sensor data to the estimation device.

5. The estimation device according to claim 1, wherein:
in a case where the attribute is the user being a woman, the predetermined sub-range of the normalized gait cycle is a female feature amount extraction period including a period immediately after heel-strike and a period of single-leg support from the gait waveform regarding an angle in the coronal plane, the training feature amount is extracted in the female feature amount extraction period, and the plurality of subjects is a plurality of female subjects, and
in a case where the attribute is the user being a male, the predetermined sub-range of the normalized gait cycle is a male feature amount extraction period including a period immediately before toe-off and a period immediately before heel-strike from the gait waveform regarding an angle in the coronal plane, the training feature amount is extracted from the male feature amount extraction period, and the plurality of subjects is a plurality of male subjects.

6. The estimation device according to claim 1, wherein:
in a case where the attribute is the user being an elderly person, the predetermined sub-range of the normalized gait cycle is an elderly person feature amount extraction period including a period immediately after heel-strike and a period immediately before heel-strike from the gait waveform regarding an angle in the coronal plane, the training feature amount is extracted in the elderly person feature amount extraction period, and the plurality of subjects is a plurality of elderly subjects, and
in a case where the attribute is the user being a young person, the predetermined sub-range of the normalized gait cycle is a young person feature amount extraction period including a period immediately before toe-off and a period immediately before heel-strike from the gait waveform regarding an angle in the coronal plane, the feature amount is extracted in the young person feature amount extraction period, and the plurality of subjects is a plurality of young subjects.

7. An estimation method executed by a computer, the method comprising:
receiving, via a communication interface, time-series sensor data including three-axis acceleration and angular velocity from a data acquisition device installed in footwear at a back-of-arch position of a foot of a user;
converting the received sensor data from a local coordinate system of the data acquisition device to a world coordinate system;
detecting gait events in the converted, received sensor data, the detected gait events including heel-strike events and toe-off events;
generating, for one gait cycle normalized between consecutive ones of the heel-strike events, a gait waveform of a pitch angle representing rotation about a Y-axis in a coronal plane;
extracting, from the pitch-angle gait waveform, a feature amount according to an attribute of the user selected from gender and age in a section defined as a predetermined sub-range of the normalized gait cycle identified relative to the detected heel-strike and toe-off events, the feature amount comprising at least one of an arithmetic mean or an integral of the pitch angle;
inputting the feature amount to an attribute-specific inference model stored in a memory, the model being trained with a data set in which a training feature amount is an explanatory variable and a center of pressure excursion index (CPEI) obtained from a foot pressure distribution measured by a pressure sensor is an objective variable for a plurality of subjects;
executing the attribute-specific inference model to estimate the CPEI for the user based on the inputted feature amount;
classifying a degree of pronation/supination of a foot of the user based on the estimated CPEI, the classification being determined using thresholds stored in the memory including a pronation threshold and a supination threshold; and
causing an output unit to present the estimated CPEI and the classification among pronation/normal/supination.

8. The estimation method according to claim 7, wherein:
in a case where the attribute is the user being a woman, the predetermined sub-range of the normalized gait cycle is a female feature amount extraction period including a period immediately after heel-strike and a period of single-leg support from the gait waveform regarding an angle in the coronal plane, the training feature amount is extracted in the female feature amount extraction period, and the plurality of subjects is a plurality of female subjects, and
in a case where the attribute is the user being a male, the predetermined sub-range of the normalized gait cycle is a male feature amount extraction period including a period immediately before toe-off and a period immediately before heel-strike from the gait waveform regarding an angle in the coronal plane, the training feature amount is extracted from the male feature amount extraction period, and the plurality of subjects is a plurality of male subjects.

9. The estimation method according to claim 7, wherein:
in a case where the attribute is the user being an elderly person, the predetermined sub-range of the normalized gait cycle is an elderly person feature amount extraction period including a period immediately after heel-strike and a period immediately before heel-strike from the gait waveform regarding an angle in the coronal plane, the training feature amount is extracted in the elderly person feature amount extraction period, and the plurality of subjects is a plurality of elderly subjects, and
in a case where the attribute is the user being a young person, the predetermined sub-range of the normalized gait cycle is a young person feature amount extraction period including a period immediately before toe-off and a period immediately before heel-strike from the gait waveform regarding an angle in the coronal plane, the training feature amount is extracted in the young person feature amount extraction period, and the plurality of subjects is a plurality of young subjects.

10. A non-transitory program recording medium storing a program for causing a computer to execute:
receiving, via a communication interface, time-series sensor data including three-axis acceleration and angular velocity from a data acquisition device installed in footwear at a back-of-arch position of a foot of a user;
converting the received sensor data from a local coordinate system of the data acquisition device to a world coordinate system;
detecting gait events in the converted, received sensor data, the detected gait events including heel-strike events and toe-off events;
generating, for one gait cycle normalized between consecutive ones of the heel-strike events, a gait waveform of a pitch angle representing rotation about a Y-axis in a coronal plane;
extracting, from the pitch-angle gait waveform, a feature amount according to an attribute of the user selected from gender and age in a section defined as a predetermined sub-range of the normalized gait cycle identified relative to the detected heel-strike and toe-off events, the feature amount comprising at least one of an arithmetic mean or an integral of the pitch angle;
inputting the feature amount to an attribute-specific inference model stored in the memory, the model being trained with a data set in which a training feature amount is an explanatory variable and a center of pressure excursion index (CPEI) obtained from a foot pressure distribution measured by a pressure sensor is an objective variable for a plurality of subjects;

executing the attribute-specific inference model to estimate the CPEI for the user based on the inputted feature amount;

classifying a degree of pronation/supination of a foot of the user based on the estimated CPEI, the classification being determined using thresholds stored in the memory including a pronation threshold and a supination threshold; and causing an output unit to present the estimated CPEI and the classification among pronation/normal/supination.

11. The non-transitory program recording medium according to claim 10, wherein:

in a case where the attribute is the user being a woman, the predetermined sub-range of the normalized gait cycle is a female feature amount extraction period including a period immediately after heel-strike and a period of single-leg support from the gait waveform regarding an angle in the coronal plane, the training feature amount is extracted in the female feature amount extraction period, and the plurality of subjects is a plurality of female subjects, and in a case where the attribute is the user being a male, the predetermined sub-range of the normalized gait cycle is a male feature amount extraction period including a period immediately before toe-off and a period immediately before heel-strike from the gait waveform regarding an angle in the coronal plane, the training feature amount is extracted from the male feature amount extraction period, and the plurality of subjects is a plurality of male subjects.

12. The non-transitory program recording medium according to claim 10, wherein the program is configured to cause the computer to execute:

in a case where the attribute is the user being an elderly person, the predetermined sub-range of the normalized gait cycle is an elderly person feature amount extraction period including a period immediately after heel-strike and a period immediately before heel-strike from the gait waveform regarding an angle in the coronal plane, the training feature amount is extracted in the elderly person feature amount extraction period, and the plurality of subjects is a plurality of elderly subjects; and in a case where the attribute is the user being a young person, the predetermined sub-range of the normalized gait cycle is a young person feature amount extraction period including a period immediately before toe-off and a period immediately before heel-strike from the gait waveform regarding an angle in the coronal plane, the training feature amount is extracted in the young person feature amount extraction period, and the plurality of subjects is a plurality of young subjects.

* * * * *